United States Patent
Hodgson et al.

(10) Patent No.: US 7,989,629 B2
(45) Date of Patent: Aug. 2, 2011

(54) 3-(4-{ [4-(4-{ [3-(3,3-DIMETHYL-1-PIPERIDINYL) PROPYL] OXY} PHENYL)-1-PIPERIDINYL] CARBONYL}-1-NAPHTHALENYL) PROPANOIC OR PROPENOIC ACID AS H1 AND H3 RECEPTOR ANTAGONISTS FOR THE TREATMENT OF INFLAMMATORY AND/OR ALLERGIC DISORDERS

(75) Inventors: Simon Teanby Hodgson, Stevenage (GB); Panayiotis Alexandrou Procopiou, Stevenage (GB); Maria Victoria Vinader Brugarolas, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 244 days.

(21) Appl. No.: 12/158,185

(22) PCT Filed: Dec. 19, 2006

(86) PCT No.: PCT/EP2006/069943
§ 371 (c)(1),
(2), (4) Date: Jun. 19, 2008

(87) PCT Pub. No.: WO2007/071691
PCT Pub. Date: Jun. 28, 2007

(65) Prior Publication Data
US 2008/0312280 A1    Dec. 18, 2008

(30) Foreign Application Priority Data

Dec. 20, 2005  (GB) .................................. 0525897.5
Nov. 21, 2006  (GB) .................................. 0623217.7

(51) Int. Cl.
C07D 211/20    (2006.01)
A61K 31/451    (2006.01)

(52) U.S. Cl. ........................................ 546/189; 514/316
(58) Field of Classification Search .................. 546/189; 514/316
See application file for complete search history.

(56) References Cited

U.S. PATENT DOCUMENTS 7,465,795 B2    12/2008  Chapdelaine et al.

FOREIGN PATENT DOCUMENTS

| WO | 2004/035556 A | 4/2004 |
|----|---------------|--------|
| WO | 2004/037800 A | 5/2004 |
| WO | 2004/089373 A1 | 10/2004 |
| WO | 2005116037 A1 | 12/2005 |
| WO | 2007/122156 A1 | 11/2007 |

OTHER PUBLICATIONS

Scadding, G. "Predicting and Establishing the Clinical Efficacy of a Histamine H1-Receptor Antagonist" Clinical Drug Investigation Mar. 1, 2005 25(3), 153-164.*
Simons, F. "Antihistamines" Middleton's Allergy: Principles and Practice Sixth edition. Chapter 51: 834-863, 2003.*
Grant R. Zimmermann "Multi-target therapeutics: when the whole is greater than the sum of the parts." Drug Discovery Today 2007, 12, 34-42.*
Borisy et. al. "Systematic discovery of multicomponent therapeutics" PNAS 2003, 100, 7977-7982.*
Sylvain Celanier, Maikel Wijtmans, Patrice Talaga, Rob Leurs, Iwan J. P. De Esch; Histamine H3 receptor Antagonists reach out for the clinic; Drug Discovery Today; Dec. 2005; 10; 1613-1627; Elsevier Science Ltd; London, UK.
McLeod et al.; "Effect of combined histamine H1 and H3 receptor blockade on cutaneous microvascular permeability elicited by compound 48/80"; Life Sciences; 2005; vol. 76, No. 16; pp. 1787-1794; Pergamon Press; Oxford, GB.

* cited by examiner

*Primary Examiner* — Janet Andres
*Assistant Examiner* — David K O'Dell
(74) *Attorney, Agent, or Firm* — James P. Riek

(57) ABSTRACT

The present invention relates to a compound of formula (I), or a salt thereof

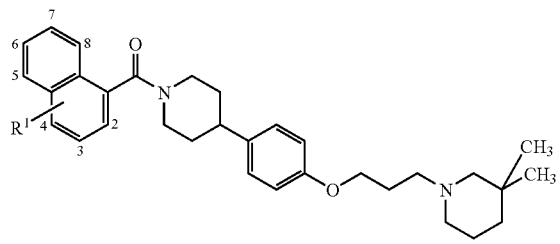

(I)

wherein the naphthalene ring is substituted in the 2, 3, 4, 5, 6, 7 or 8 position by $R^1$, and $R^1$ represents —$CH_2CH_2COOH$ or —$CH=C(CH_3)COOH$, and to processes for their preparation, to compositions containing them and to their use in the treatment of various inflammatory and/or allergic diseases, such as diseases such as allergic rhinitis.

16 Claims, 2 Drawing Sheets

Figure 1: XRPD pattern for the hydrochloride salt of 3-(4-{[4-(4-{[3-(3,3-dimethyl-1-piperidinyl)propyl]oxy}phenyl)-1-piperidinyl]carbonyl}-1-naphthalenyl)propanoic acid (Example 3)
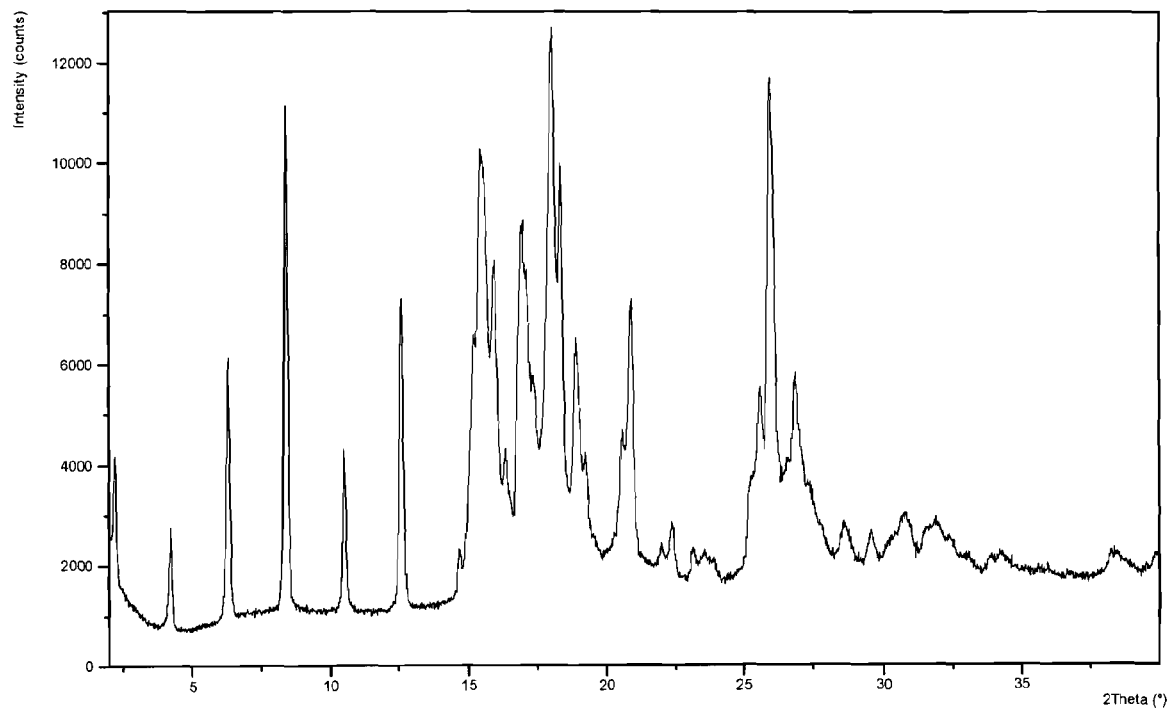

Figure 2: DSC thermogram of the hydrochloride salt of 3-(4-{[4-(4-{[3-(3,3-dimethyl-1-piperidinyl)propyl]oxy}phenyl)-1-piperidinyl]carbonyl}-1-naphthalenyl)propanoic acid (Example 3). Observed events: Endotherm with onset temperature of approximately 164 °C, due to sample melt.
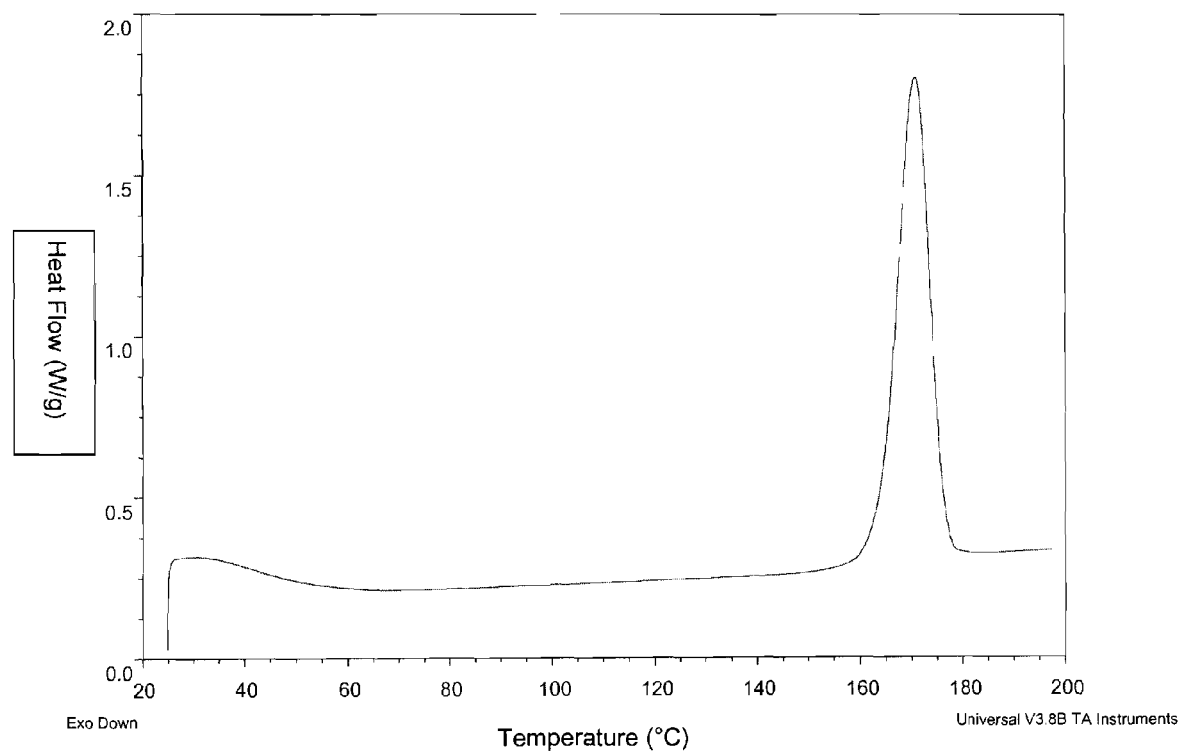

3-(4-{[4-(4-{[3-(3,3-DIMETHYL-1-PIPERIDINYL) PROPYL]OXY} PHENYL)-1-PIPERIDINYL] CARBONYL}-1-NAPHTHALENYL) PROPANOIC OR PROPENOIC ACID AS H1 AND H3 RECEPTOR ANTAGONISTS FOR THE TREATMENT OF INFLAMMATORY AND/OR ALLERGIC DISORDERS

CROSS-REFERENCE TO RELATED APPLICATIONS

This application is filed pursuant to 35 USC 371 as a United States National Phase Application of International Patent Application Serial No. PCT/EP2006/069943 filed on 19 Dec. 2006, which claims priority from GB 0525897.5 filed on 20 Dec. 2005 in the United Kingdom and GB 0623217.7 filed on 21 Nov. 2006 in the United Kingdom.

The present invention relates to compounds, processes for their preparation, pharmaceutical compositions containing them and to their use in the treatment of various diseases, in particular inflammatory and/or allergic diseases of the respiratory tract.

Allergic rhinitis, pulmonary inflammation and congestion are medical conditions that are often associated with other conditions such as asthma, chronic obstructive pulmonary disease (COPD), seasonal allergic rhinitis and perennial allergic rhinitis. In general these conditions are mediated, at least in part, by inflammation associated with the release of histamine from various cells, in particular mast cells.

Allergic rhinitis, also known as 'hay fever', affects a large proportion of the population worldwide. There are two types of allergic rhinitis, seasonal and perennial. The clinical symptoms of seasonal allergic rhinitis typically include nasal itching and irritation, sneezing and watery rhinorrhea which is often accompanied by nasal congestion. The clinical symptoms of perennial allergic rhinitis are similar except that nasal blockage may be more pronounced. Either type of allergic rhinitis may also cause other symptoms such as itching of the throat and/or eyes, epiphora and oedema around the eyes. The symptoms of allergic rhinitis may vary in intensity from the nuisance level to debilitating.

Allergic rhinitis and other allergic conditions are associated with the release of histamine from various cell types, but particularly mast cells. The physiological effects of histamine are classically mediated by three receptor subtypes, termed H1, H2 and H3. H1 receptors are widely distributed throughout the CNS and periphery, and are involved in wakefulness and acute inflammation. H2 receptors mediate gastric acid secretion in response to histamine. H3 receptors are present on the nerve endings in both the CNS and periphery and mediate inhibition of neurotransmitter release [Hill et al., Pharmacol. Rev., 49:253-278, (1997)]. Recently a fourth member of the histamine receptor family has been identified, termed the H4 receptor [Hough, Mol. Pharmacol., 59:415-419, (2001)]. Whilst the distribution of the H4 receptor appears to be restricted to cells of the immune and inflammatory systems, a physiological role for this receptor remains to be clarified.

The activation of H1 receptors in blood vessels and nerve endings is responsible for many of the symptoms of allergic rhinitis, which include itching, sneezing, and the production of watery rhinorrhea. Antihistamine compounds, i.e. drugs which are selective H1 receptor antagonists such as chlorphenyramine and cetirizine, are effective in treating the itching, sneezing and rhinorrhea associated with allergic rhinitis, but are not effective against the nasal congestion symptoms [Aaronson, Ann. Allergy, 67:541-547, (1991)]. Thus H1 receptor antagonists have been administered in combination with sympathomimetic agents such as pseudoephedrine or oxymetazoline to treat the nasal congestion symptoms of allergic rhinitis. These drugs are thought to produce a decongestant action by activating β-adrenergic receptors and increasing the vascular tone of blood vessels in the nasal mucosa. The use of sympathomimetic drugs for the treatment of nasal congestion is frequently limited by the CNS stimulant properties and their effects on blood pressure and heart rate. A treatment which decreases nasal congestion without having effects on the CNS and cardiovascular system may therefore offer advantages over existing therapies.

Histamine H3 receptors are expressed widely on both CNS and peripheral nerve endings and mediate the inhibition of neurotransmitter release. In vitro electrical stimulation of peripheral sympathetic nerves in isolated human saphenous vein results in an increase in noradrenaline release and smooth muscle contraction, which can be inhibited by histamine H3 receptor agonists [Molderings et al., Naunyn-Schmiedeberg's Arch. Pharmacol., 346:46-50, (1992); Valentine et al., Eur. J. Pharmacol., 366:73-78, (1999)]. H3 receptor agonists also inhibit the effect of sympathetic nerve activation on vascular tone in porcine nasal mucosa [Varty & Hey., Eur. J. Pharmacol., 452:339-345, (2002)]. In vivo, H3 receptor agonists inhibit the decrease in nasal airway resistance produced by sympathetic nerve activation [Hey et al., Arzneim-Forsch Drug Res., 48:881-888, (1998)]. Activation of histamine H3 receptors in human nasal mucosa inhibits sympathetic vasoconstriction [Varty et al., Eur. J. Pharmacol., 484:83-89, (2004)]. Furthermore, H3 receptor antagonists, in combination with histamine H1 receptor antagonists, have been shown to reverse the effects of mast cell activation on nasal airway resistance and nasal cavity volume, an index of nasal congestion [Mcleod et al., Am. J. Rhinol., 13:391-399, (1999)], and further evidence for the contribution of H3 receptors to histamine-induced nasal blockage is provided by histamine nasal challenge studies performed on normal human subjects [Taylor-Clark et al., Br. J. Pharmacol., 144, 867-874, (2005)], although the H3 mechanism in this regard would appear to be novel and unprecedented.

A novel class of compounds has been found that are dual histamine H1 and H3 receptor antagonists. By 'dual' histamine H1 and H3 receptor antagonists it is meant that the compound has activity at both receptor subtypes. In particular the activity at the H1 receptor may be within approximately 10 fold of the activity at the H3 receptor and more particularly such compounds may be approximately equipotent at both receptor subtypes.

Thus, the present invention provides, in a first aspect, a compound of formula (I)

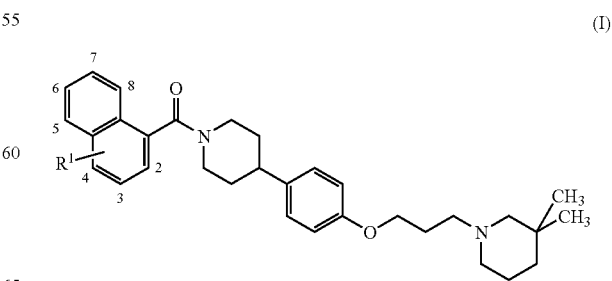

(I)

wherein the naphthalene ring is substituted in the 2, 3, 4, 5, 6, 7 or 8 position by $R^1$, and $R^1$ represents —CH$_2$CH$_2$COOH or —CH=C(CH$_3$)COOH;

or a salt thereof, such as a pharmaceutically acceptable salt.

The compounds of the invention may be expected to be useful in the treatment of various disorders, in particular inflammatory and/or allergic disorders, such as inflammatory and/or allergic disorders of the respiratory tract, for example allergic rhinitis, that are associated with the release of histamine from cells such as mast cells.

The compounds of the invention may show an improved profile over known dual H1/H3 receptor antagonists agonists in that they may possess one or more of the following properties:

(i) H3 receptor antagonist activity with a pKi of greater than about 7;
(ii) H1 receptor antagonist agonist activity with a pKi of greater than 7;
(iii) lower CNS penetration;
(iv) improved bioavailability; and
(v) lower clearance and/or longer half-life in blood.

Compounds having such a profile may be expected to be orally effective, and/or capable of once daily administration and/or further may have an improved side effect profile compared with other existing therapies.

In one embodiment of the invention, $R^1$ represents —CH$_2$CH$_2$COOH.

In another embodiment of the invention, the naphthalene ring is substituted in the 4 position by $R^1$.

Compounds of formula (I) include the compound of the Examples as described below and salts thereof, such as pharmaceutically acceptable salts.

Thus, in a further aspect the present invention provides a compound 3-(4-{[4-(4-{[3-(3,3-dimethyl-1-piperidinyl)propyl]oxy}phenyl)-1-piperidinyl]carbonyl}-1-naphthalenyl)propanoic acid or a salt thereof, such as a pharmaceutically acceptable salt.

It is to be further understood that references hereinafter to a compound according to the invention or to compounds of the invention includes one or more compounds of formula (I) and salts thereof, such as pharmaceutically acceptable salts.

The present invention encompasses geometric isomers of the compounds of formula (I) including cis and trans configurations, and regioisomers including exo and endo double bonds (e.g. —CH=C(CH$_3$)COOH and —CH—C(=CH$_2$)COOH), whether as individual isomers isolated such as to be substantially free of the other isomers (i.e. pure) or as mixtures thereof. Thus for example the present invention encompasses an individual isomer isolated such as to be substantially free of the other isomer (i.e. pure) such that less than 10%, for example less than 1% or less than 0.1% of the other isomer is present. Separation of geometric isomers may be achieved by conventional techniques, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

The compounds of formula (I) may be in crystalline or amorphous form. Furthermore, a compound of formula (I) may exist in one or more polymorphic forms. Thus, the present invention includes within its scope all polymorphic forms of the compounds of formula (I). In general, the most thermodynamically stable polymorphic form of a compound of formula (I) is of particular interest.

Polymorphic forms of compounds of formula (I) may be characterized and differentiated using a number of conventional analytical techniques, including but not limited to X-ray powder diffraction (XRPD) patterns, infrared (IR) spectra, Raman spectra, differential scanning calorimetry (DSC), thermogravimetric analysis (TGA) and solid state nuclear magnetic resonance (NMR).

It will be appreciated that many organic compounds can form solvates with the solvents in which they are reacted or from which they are precipitated or crystallized. For example, a solvate with water is known as a "hydrate". Solvents with high boiling points and/or solvents with a high propensity to form hydrogen bonds such as water, xylene, N-methyl pyrrolidinone and methanol may be used to form solvates. Methods for identification of solvates include, but are not limited to, NMR and microanalysis. Thus, solvates of the compounds of formula (I) are within the scope of the invention.

The compounds of the present invention may be in the form of and/or may be administered as a pharmaceutically acceptable salt. For a review on suitable salts see Berge et al., J. Pharm. Sci., 1977, 66, 1-19. Suitable pharmaceutically acceptable salts include acid and base addition salts.

Typically, a pharmaceutically acceptable salt may be readily prepared by using a desired acid or base as appropriate. The salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, formic, sulfuric, nitric, phosphoric, succinic, maleic, acetic, fumaric, citric, tartaric, benzoic, p-toluenesulfonic, methanesulfonic or naphthalenesulfonic acid), optionally in a suitable solvent such as an organic solvent, to give the salt which is usually isolated for example by crystallisation and filtration. Thus, a pharmaceutically acceptable acid addition salt of a compound of formula (I) can be for example a hydrobromide, hydrochloride, formate, sulfate, nitrate, phosphate, succinate, maleate, acetate, fumarate, citrate, tartrate, benzoate, p-toluenesulfonate, methanesulfonate or naphthalenesulfonate salt.

In one embodiment, there is provided a hydrochloride salt of the compound 3-(4-{[4-(4-{[3-(3,3-dimethyl-1-piperidinyl)propyl]oxy}phenyl)-1-piperidinyl]carbonyl}-1-naphthalenyl)propanoic acid.

In another embodiment, there is provided a hydrobromide salt of the compound 3-(4-{[4-(4-{[3-(3,3-dimethyl-1-piperidinyl)propyl]oxy}phenyl)-1-piperidinyl]carbonyl}-1-naphthalenyl)propanoic acid.

A pharmaceutically acceptable base addition salt can be formed by reaction of a compound of formula (I) with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in the compound of formula (I).

Other non-pharmaceutically acceptable salts, eg. oxalates or trifluoroacetates, may be used, for example in the isolation of compounds of the invention, and are included within the scope of this invention. The invention includes within its scope all possible stoichiometric and non-stoichiometric forms of the salts of the compounds of formula (I).

Included within the scope of the invention are all solvates e.g. hydrates and polymorphs of compounds and salts of the invention.

The present invention also provides processes for the preparation of a compound of formula (I) or a salt thereof.

According to first process (A), a compound of formula (I) may be prepared by deprotecting and optionally hydrogenating a compound of formula (Ia)

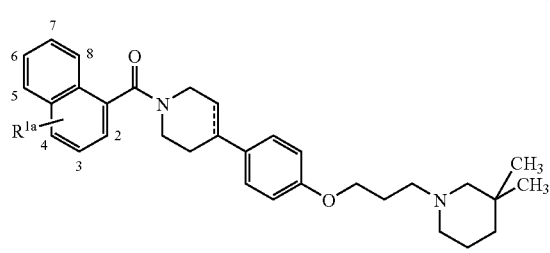

(Ia)

wherein

---- represents a single or a double bond, and the naphthalene ring is substituted in the 2, 3, 4, 5, 6, 7, 8 position by $R^{1a}$, and $R^{1a}$ represents a protected derivative of $R^1$ such as an ester of $R^1$, for example, —$CH_2CH_2COOR^x$ or —CH=C($CH_3$)$COOR^x$ in which each $R^x$ independently represents a carboxylic acid protecting group such $C_1$-$C_6$ alkyl, for example, methyl, ethyl or t-butyl, especially methyl or ethyl. Other suitable protecting groups include aralkyl such as benzyl.

Deprotection may be performed under standard conditions. Thus, hydrolysis of a carboxylic acid ester may be performed in the presence of a suitable base, for example, sodium hydroxide or potassium hydroxide, in a suitable aqueous solvent system such as methanol/water or tetrahydrofuran/water, optionally at an elevated temperature such as reflux. Alternatively, hydrolysis of a carboxylic acid ester, for example, the t-butyl ester may be performed in the presence of a suitable acid such as hydrogen chloride in dioxane under standard conditions for acid hydrolysis. Deprotection by hydrogenolysis under standard conditions, such as in the presence of a metal catalyst such as palladium-on-charcoal may be employed when the protecting group is aralkyl such as benzyl.

Hydrogenation may be performed under standard conditions. Thus, hydrogenation may be performed in the presence of a suitable hydrogenation agent such as palladium on carbon or platinum oxide in a suitable solvent such as ethanol, optionally at atmospheric pressure, and optionally at an elevated temperature such as 40 to 60° C.

In one embodiment of process A, $R^{1a}$ is as defined, and ---- represents a single bond in which case a hydrogenation step is not required.

Compounds of formula (Ia) may be prepared by reacting a compound of formula (II)

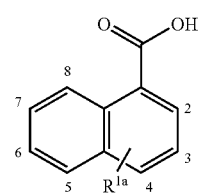

(II)

wherein $R^{1a}$ is as defined above for formula (Ia), with a compound of formula (III)

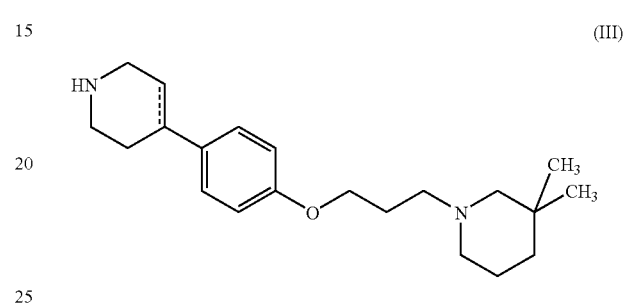

(III)

wherein ---- represents a single or a double bond, under amide forming conditions.

The amide of formula (Ia) may be prepared under standard conditions for amide coupling, for example in the presence of a suitable coupling agent such as O-(benzotriazol-1-yl)-N,N,N',N'-tetramethyluronium hexafluorophosphate (HBTU) or O-(benzotriazol-1-yl)-N,N,N',N'-tetramethyluronium tetrafluoroborate (TBTU), in the presence of a suitable base such as triethylamine, in an appropriate solvent such as N,N-dimethylformamide.

Alternatively compound (Ia) may be prepared by reacting an acid chloride of a compound of formula (II) with an amine (III) in the presence of a suitable base, such as triethylamine or potassium carbonate, in a solvent such as dichloromethane at a temperature between 0 and 20° C.

A compound of formula (II) wherein $R^{1a}$ represents —$CH_2CH_2COOR^x$ and $R^x$ is as defined above may be prepared by hydrogenation of a compound of formula (IV)

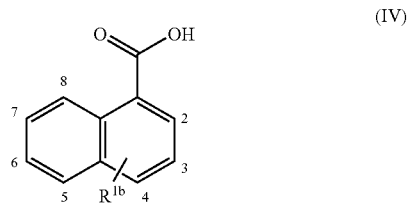

(IV)

wherein the naphthalene ring is substituted in the 2, 3, 4, 5, 6, 7 or 8 position by $R^{1b}$, and $R^{1b}$ represents —CH=CH—$COOR^x$ and $R^x$ is as defined above.

Hydrogenation is performed under standard conditions. Thus, hydrogenation may be performed in the presence of a suitable hydrogenation agent such as palladium on carbon or platinum oxide in a suitable solvent such as ethanol, optionally at atmospheric pressure, and optionally at an elevated temperature such as 40 to 60° C.

A compound of formula (IV) as defined above may be prepared by a Heck reaction in which a compound of formula (V) or a protected derivative thereof

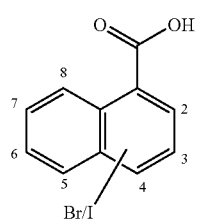

wherein the naphthalene ring is substituted in the 2, 3, 4, 5, 6, 7 or 8 position by bromine or iodine, is reacted with an acrylate ester such as methyl acrylate, ethyl acrylate, t-butyl acrylate and benzyl acrylate.

It will be appreciated by those skilled in the art that the Br/I substituent will be in the position at which it is desired to introduce the carboxylate group in the compound of formula (IV).

Generally, the Heck reaction may be carried out in the presence of a suitable base such as triethylamine, a phosphine such as triphenylphosphine, a suitable catalyst such as palladium (II) acetate, in a suitable solvent such as N,N-dimethylformamide, at an elevated temperature, for example about 100° C.

In an alternative method, a compound of formula (IV) described above may be prepared by a Wittig reaction in which a corresponding compound of formula (VI)

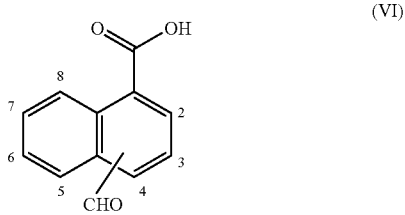

wherein the naphthalene ring is substituted in the 2, 3, 4, 5, 6, 7 or 8 position by CHO, is reacted with a phosphorus ylid containing a carboalkoxymethylene group (—CH—COOR$^x$ wherein R$^x$ represents C$_{1-6}$ alkyl) such as carboethoxymethylene-triphenylphosphorane, in a suitable solvent such as toluene, at an elevated temperature such as reflux.

Compounds of formula (II) wherein R$^{1a}$ represents —CH=C(CH$_3$)COOR$^x$ and R$^x$ is as defined above may be prepared by a Heck reaction in which a compound of formula (V) or a protected derivative thereof is reacted with an acrylate ester such as methyl methacrylate, ethyl methacrylate or t-butyl methacrylate, under similar conditions to the Heck reaction described above.

Alternatively, a compound of formula (II) wherein R$^{1a}$ represents —CH=C(CH$_3$)COOR$^x$ and R$^x$ is as defined above may be prepared by a Wittig reaction in which a compound or formula (VI) as described above is reacted with a phosphorus ylid containing a carboalkoxymethylene group (—CH—COOR$^x$ wherein R$^x$ represents C$_{1-6}$ alkyl) such as carboethoxyethylene-triphenylphosphorane, under similar conditions to the Wittig reaction described above.

Compounds of formula (V) and (VI) are known, or may be prepared from commercially available materials (for example 1,4-dibromonaphthalene is commercially available from Acros and/or Alfa) in accordance with published methods or by the methods described herein. 5-bromo-1-naphthalenecarboxylic acid may be prepared by the methods described in J. E. Baldwin, et al., Tetrahedron 1990, 46, 3019-28, 4-bromo-1-naphthalenecarboxylic acid may be prepared by the methods described in Can. J. Chem. 1981, 59, 2629-41; and 8-formyl-1-naphthalenecarboxylic acid may be prepared by the methods described in J. Am. Chem. Soc., 1949, 71, 1870.

Acrylate esters are known and/or are commercially available. Methyl acrylate, methyl methacrylate and benzylacrylate are available from Aldrich and/or Acros and/or ABCR and/or Chemos.

Compounds of formula (III) may be prepared according to the following reaction scheme:

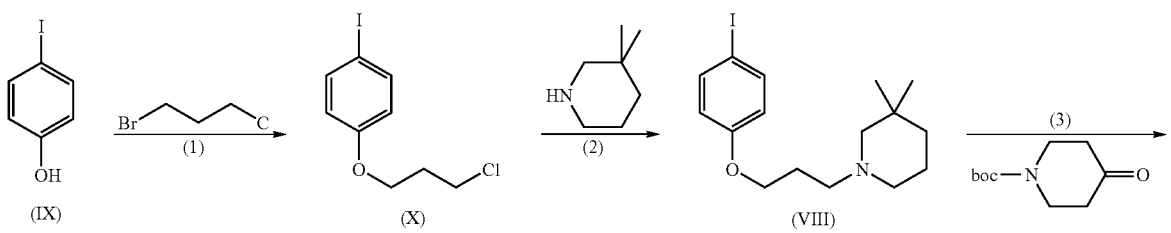

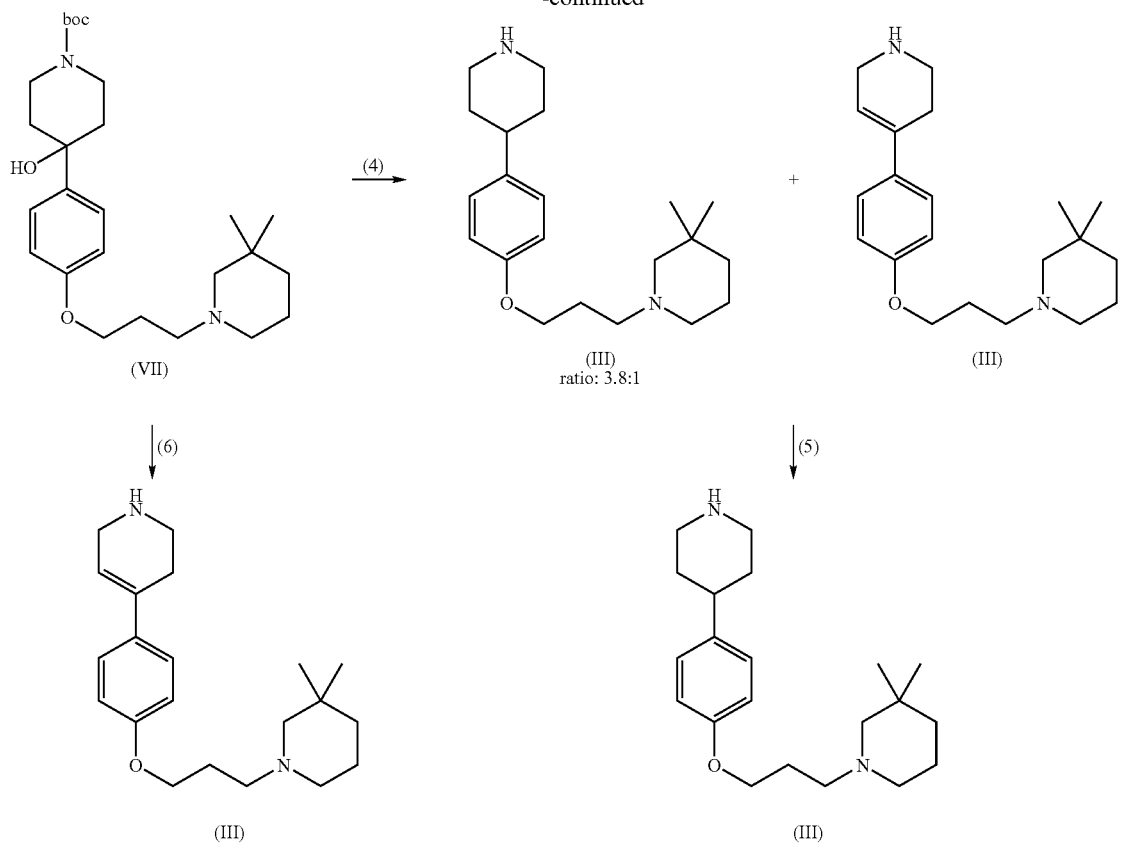

in which
1. potassium carbonate, 2-butanone;
2. sodium iodide, potassium carbonate, acetonitrile;
3. nBuLi, THF. Alternatively, iso-propyl magnesium chloride may be used instead of nBuLi at ambient temperature;
4. a) triethylsilane, trifluoroacetic acid, dichloromethane; b) 2M HCl in ether, to give a mixture of compounds of formula (III);
5. optional hydrogenation step, 10% wt palladium on carbon ethanol.
6. hydrogen chloride, ethanol.

It will be appreciated that the mixture of compounds of formula (III) shown above may be used in subsequent reactions without the need to perform the hydrogenation step 5.

4-Iodophenol, 1-bromochloropropane, 3,3-dimethyl piperidine, and N-Boc-piperidone are known and/or commercially available, for example from Aldrich, Alfa, Manchester Organics, Matrix Scientific, ASDI and/or Chem. Service.

According to a second process (B) a compound of formula (I) may be prepared by:
(i) reacting a compound of formula (II) with a compound of formula (III) to form a compound of formula (Ia); and
(ii) deprotecting and optionally dehydrogenating the compound of formula (Ia) to form a compound of formula (I).

In process (B) the intermediate protected amide for example the amide ester (Ia) is not isolated. Amide coupling and deprotection, such as by carboxylic acid ester hydrolysis, and optional hydrogenation may be performed under standard conditions as described above.

According to a third process (C) a compound of formula (I) wherein $R^1$ represents —$CH_2CH_2COOH$ may be prepared by hydrogenating and deprotecting a compound of formula (Ic)

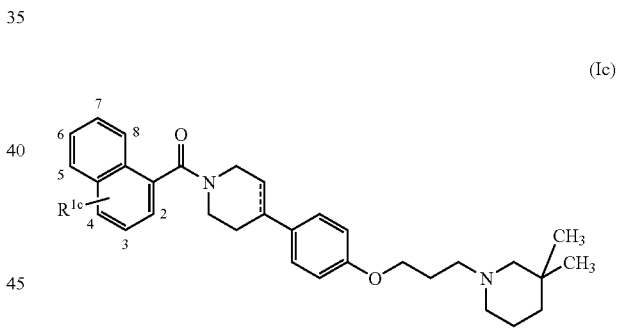

wherein
----- represents a single or a double bond, and the naphthalene ring can be substituted in the 2, 3, 4, 5, 6, 7 or 8 position by $R^{1c}$ and $R^{1c}$ represents —$CH=CHCOOR^x$ wherein $R^x$ represents a suitable carboxylic acid protecting group such as aralkyl e.g. benzyl. Hydrogenation and deprotection (by hydrogenolysis) may be performed under standard conditions such as those that are described herein, and may be combined in a single step.

A compound of formula (Ic) may be prepared by reacting a compound of formula (IV) with a compound of formula (III).

According to a fourth process (D), a compound of formula (I) may be prepared by interconversion from other compounds of formula (I). Thus, a compound of formula (I) may also be prepared from other compounds of formula (I) using conventional interconversion procedures such as isomerisation of geometric isomers e.g. interconversion between cis and trans isomers and interconversion between an exo and endo double bond, for example, interconversion between —CH═C(CH₃)COOH and —CH₂—C(═CH₂)COOH. It may also include procedures to change the counterion and salt form of a compound of formula (I). Thus, interconversion from other compounds of formula (I) (process D) forms yet a further aspect of the present invention.

Thus, the present invention provides a process for preparing a compound of formula (I) or a salt thereof, the process selected from (A), (B), (C) or (D) herein, and optionally thereafter forming a salt.

Typically, a salt may readily be prepared using a desired acid or base as appropriate. The salt may precipitate from solution and be collected by filtration or may be recovered by evaporation of the solvent. It is to be understood that the free base of a compound of formula (I) may or may not be isolated prior to salt formation, as desired.

It will be appreciated by those skilled in the art that it may be desirable to use protected derivatives of intermediates used in the preparation of compounds of formula (I). Thus, the above processes may require deprotection as an intermediate step or final step to yield the desired compound. Protection and deprotection of functional groups may be effected using conventional means. Thus, carboxylic acid groups may be protected using any conventional protecting groups, for example, as described in Protective Groups in Organic Chemistry, Ed. J. F. W. McOmie (Plenum Press, 1973) or Protective Groups in Organic Synthesis by Theodora W. Green (John Wiley and Sons, 1991) or P. J. Kocienski in Protecting Groups, Georg Thieme Verlag 1994.

Examples of suitable carboxylic acid protecting groups include groups selected from alkyl (e.g. methyl, ethyl or t-butyl), aralkyl (e.g. benzyl, diphenylmethyl or triphenylmethyl), and silyl groups such as trialkylsilyl (e.g. t-butyldimethylsilyl). The carboxylic acid protecting groups may be removed by conventional techniques. Thus, for example alkyl and silyl groups, may be removed by solvolysis, e.g. by hydrolysis under acidic or basic conditions. Aralkyl groups such as triphenylmethyl may be similarly be removed by solvolysis, e.g. by hydrolysis under acidic conditions. Aralkyl groups such as benzyl may be cleaved by hydrogenolysis in the presence of a metal catalyst such as palladium-on-charcoal.

Examples of disease states in which a compound of formula (I), or a pharmaceutically acceptable salt thereof may be expected to have beneficial anti-inflammatory and/or anti-allergic effects include diseases of the respiratory tract such as bronchitis (including chronic bronchitis), asthma (including allergen-induced asthmatic reactions), chronic obstructive pulmonary disease (COPD), cystic fibrosis, sinusitis and allergic rhinitis (seasonal and perennial). Other disease states include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure.

Furthermore, compounds of the invention may be used to treat nephritis, skin diseases such as psoriasis, eczema, allergic dermatitis and hypersensitivity reactions.

Compounds of the invention may also be of use in the treatment of nasal polyposis, conjunctivitis or pruritis.

Further diseases include inflammatory diseases of the gastrointestinal tract such as inflammatory bowel disease.

A disease of particular interest is allergic rhinitis.

Compounds that are antagonists of the H3 receptor may also be of use in other diseases such as non-allergic rhinitis.

It will be appreciated by those skilled in the art that references herein to treatment or therapy extend to prophylaxis as well as the treatment of established conditions.

As mentioned above, compounds of formula (I) or pharmaceutically acceptable salts thereof are useful as therapeutic agents.

There is thus provided, as a further aspect of the invention, a compound of formula (I) or a pharmaceutically acceptable salt thereof for use in therapy.

According to another aspect of the invention, there is provided the use of a compound of formula (I) or a pharmaceutically acceptable salt thereof for the manufacture of a medicament for the treatment of any of the above diseases.

In a further aspect there is provided a method for the treatment of any of the above diseases, in a human or animal subject in need thereof, which method comprises administering an effective amount of a compound of formula (I) or a pharmaceutically acceptable salt thereof.

When used in therapy, the compounds of formula (I) are usually formulated in a suitable pharmaceutical composition. Such pharmaceutical compositions can be prepared using standard procedures.

Thus, the present invention further provides a composition which comprises a compound of formula (I) or a pharmaceutically acceptable salt thereof optionally with one or more pharmaceutically acceptable carriers and/or excipients.

A composition of the invention, which may be prepared by admixture, suitably at ambient temperature and atmospheric pressure, may be adapted for oral, parenteral, rectal or intranasal administration and, as such, may be in the form of tablets, capsules, liquid preparations e.g. oral liquid preparations, powders, granules, lozenges, reconstitutable powders, injectable or infusible solutions or suspensions or suppositories. Suitable compositions may be prepared according to methods well known in the art for each particular type of composition.

Compositions suitable for oral administration are of particular interest.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

For intranasal administration, suitable compositions may optionally contain one or more suspending agents, one or more preservatives, one or more wetting agents and/or one or more isotonicity adjusting agents Examples of suspending agents include carboxymethylcellulose, veegum, tragacanth, bentonite, methylcellulose and polyethylene glycols, e.g. microcrystalline cellulose or carboxy methylcellulose sodium.

For stability purposes, the composition of the present invention may be protected from microbial contamination and growth by inclusion of a preservative. Examples of pharmaceutically acceptable anti-microbial agents or preservatives may include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Compositions, e.g. nasal compositions which contain a suspended medicament may include a pharmaceutically acceptable wetting agent which functions to wet the particles of medicament to facilitate dispersion thereof in the aqueous phase of the composition. Typically, the amount of wetting agent used will not cause foaming of the dispersion during mixing. Examples of wetting agents include fatty alcohols, esters and ethers, such as polyoxyethylene (20) sorbitan monooleate (Polysorbate 80).

An isotonicity adjusting agent may be included to achieve isotonicity with body fluids eg fluids of the nasal cavity, resulting in reduced levels of irritancy. Examples of isotonicity adjusting agents include sodium chloride, dextrose and calcium chloride.

The intranasal compositions of the present invention may be administered to the nasal passages by use of a pre-compression pump, such as a VP3, VP7 or modifications, model manufactured by Valois SA. Pumps of this type are believed to be beneficial as they may ensure that the composition is not released or atomised until a sufficient force has been applied, otherwise smaller doses may be applied. Typically, these pre-compression pumps may be used with a bottle (glass or plastic) capable of holding 8-50 ml of composition and each spray will typically deliver 50-100 μL.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. A surfactant or wetting agent may be included in the composition to facilitate uniform distribution of the compound.

The composition may contain from about 0.1% to 99% by weight, such as from about 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be about 0.05 to 1000 mg, more suitably about 1.0 to 200 mg, for example 20 to 100 mg, and such unit doses may be administered more than once a day, for example two or three a day. Such therapy may extend for a number of weeks or months. In one embodiment compounds and pharmaceutical compositions according to the invention are suitable for oral administration and/or are capable of once daily administration, for example at a dose in the range of 20 to 200 mg (e.g. about 20 to 100 mg).

The compounds and pharmaceutical compositions according to the invention may also be used in combination with or include one or more other therapeutic agents, for example other antihistaminic agents for example H4 receptor antagonists, anticholinergic agents, anti-inflammatory agents such as corticosteroids (e.g. fluticasone propionate, beclomethasone dipropionate, mometasone furoate, triamcinolone acetonide, budesonide and the steroid disclosed in WO02/12265); or non-steroidal anti-inflammatory drugs (NSAIDS) (e.g. sodium cromoglycate, nedocromil sodium), PDE-4 inhibitors, leukotriene antagonists, lipoxygenase inhibitors, chemokine antagonists (e.g. CCR3, CCR1, CCR2, CCR4, CCR8, CXCR1, CXCR2), IKK antagonists, iNOS inhibitors, tryptase and elastase inhibitors, beta-2 integrin antagonists and adenosine 2a agonists; or beta adrenergic agents (e.g. salmeterol, salbutamol, formoterol, fenoterol, terbutaline, and the beta agonists described in WO 02/66422, WO 02/270490, WO02/076933, WO03/024439 and WO03/072539 and salts thereof); or antiinfective agents e.g. antibiotic agents and antiviral agents. It will be clear to a person skilled in the art that, where appropriate, the other therapeutic agent(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic agent. It will be clear also that where appropriate, the therapeutic agents may be used in optically pure form.

The invention thus provides, in a further aspect, a combination comprising a compound of formula (I) or a pharmaceutically acceptable salt thereof together with one or more (such as one or two, e.g. one) other therapeutically active agents, optionally with one or more pharmaceutically acceptable carriers and/or excipients.

Other histamine receptor antagonists which may be used alone, or in combination with a dual H1/H3 receptor antagonist include antagonists (and/or inverse agonists) of the H4 receptor, for example, the compounds disclosed in Jablonowski et al., *J. Med. Chem.* 46:3957-3960 (2003).

In one embodiment, the invention provides a combination comprising a compound of formula (I) and a $\beta_2$-adrenoreceptor agonist.

Examples of $\beta_2$-adrenoreceptor agonists include salmeterol (which may be a racemate or a single enantiomer, such as the R-enantiomer), salbutamol (which may be a racemate or a single enantiomer such as the R-enantiomer), formoterol (which may be a racemate or a single diastereomer such as the R,R-diastereomer), salmefarnol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, combinations of the invention may include longer-acting $\beta_2$-adrenoreceptor agonists, for example, compounds which provide effective bronchodilation for about 12 hours or longer.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

In another embodiment, the invention provides a combination comprising a compound of formula (I) and an adenosine 2a agonist.

A2a agonists include those disclosed in international patent application no. PCT/EP/2005/005651, such as (2R,3R, 4S,5R,2'R,3'R,4'S,5'R)-2,2'-{trans-1,4-cyclohexanediylbis [imino(2-{[2-(1-methyl-1H-imidazol-4-yl)ethyl]amino}-9H-purine-6,9-diyl)]}bis[5-(2-ethyl-2H-tetrazol-5-yl) tetrahydro-3,4-furandiol].

In another embodiment, the invention provides a combination comprising a compound of formula (I) and an anti-inflammatory agent.

Anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydrofuran-3S-yl)ester, 6α,9α-difluoro-11β-hydroxy-16α-methyl-3-oxo-17α-(2,2,3,3-tetramethycyclopropylcarbonyl) oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Corticosteroids of particular interest may include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester and mometasone furoate. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester or mometasone furoate.

Non-steroidal compounds having glucocorticoid agonism that may possess selectivity for transrepression over transactivation and that may be useful in combination therapy include those covered in the following patent application and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO0/66590, WO03/086294, WO04/026248, WO03/061651, WO03/08277, WO06/000401, WO06/000398 and WO06/015870.

Anti-inflammatory agents include non-steroidal anti-inflammatory drugs (NSAID's).

NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (eg. montelukast), iNOS (inducible nitric oxide synthase) inhibitors (e.g. oral iNOS inhibitors), IKK antagonists, tryptase and elastase inhibitors, beta-2 integrin antagonists and adenosine receptor agonists or antagonists (e.g. adenosine 2a agonists), cytokine antagonists (e.g. chemokine antagonists, such as a CCR1, CCR2, CCR3, CCR4, or CCR8 antagonists) or inhibitors of cytokine synthesis, or 5-lipoxygenase inhibitors. iNOS inhibitors include those disclosed in WO93/13055, WO98/30537, WO02/50021, WO95/34534 and WO99/62875.

In one embodiment the invention provides the use of the compounds of formula (I) in combination with a phosphodiesterase 4 (PDE4) inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds which may be of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996.

Other PDE4 inhibitors include AWD-12-281 from Elbion (Hofgen, N. et al., 15th EFMC Int. Symp. Med. Chem., (September 6-10, Edinburgh) 1998, Abst. P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al., Eur. Resp. J. [Ann. Cong. Eur. Resp. Soc. (September 19-23, Geneva) 1998] 1998, 12 (Suppl. 28): Abst P2393); roflumilast (CAS reference No 162401-32-3) and a pthalazinone (WO99/47505) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/U1M565 from Vernalis; or T-440 (Tanabe Seiyaku; Fuji, K. et al., J. Pharmacol. Exp. Ther., 284(1):162, (1998)), and T2585.

Further compounds which may be of interest are disclosed in the published international patent applications WO04/024728 (Glaxo Group Ltd), WO04/056823 (Glaxo Group Ltd) and WO04/103998 (Glaxo Group Ltd).

In yet another embodiment, the invention provides a combination comprising a compound of formula (I) and an anticholinergic agent.

Anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Other anticholinergic agents include compounds of formula (XXI), which are disclosed in U.S. patent application 60/487,981:

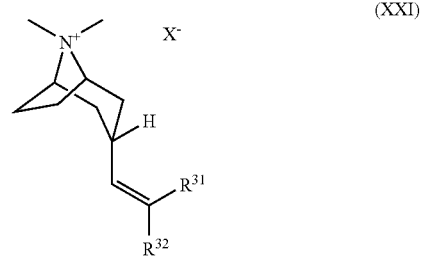

(XXI)

in which a particular orientation of the alkyl chain attached to the tropane ring is endo;
$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds of formula (XXII) or (XXIII), which are disclosed in U.S. patent application 60/511,009:

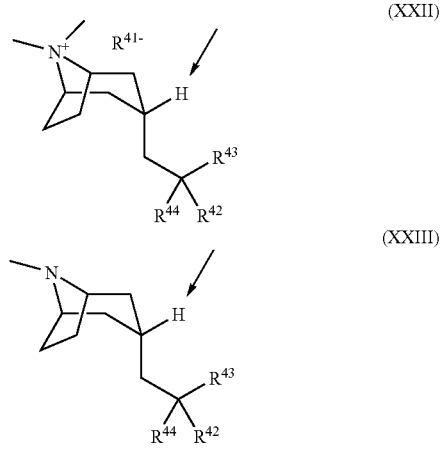

wherein:
the H atom indicated is in the exo position;
$R^{41-}$ represents an anion associated with the positive charge of the N atom. $R1^-$ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;
$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, $-OR^{45}$, $-CH_2OR^{45}$, $-CH_2OH$, $-CN$, $-CF_3$, $-CH_2O(CO)R^{46}$, $-CO_2R^{47}$, $-CH_2NH_2$, $-CH_2N(R^{47})SO_2R^{45}$, $-SO_2N(R^{47})(R^{48})$, $CON(R^{47})(R^{48})$, $-CH_2N(R^{48})CO(R^{46})$, $-CH_2N(R^{48})SO_2(R^{46})$, $-CH_2N(R^{48})CO_2(R^{45})$, $CH_2N(R^{48})CONH(R^{47})$;
$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;
$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(Endo)-3-(2-methoxy-2,2-di-thiophen-2-yl-ethyl)-8,8-dimethyl-8-azonia-bicyclo[3.2.1]octane iodide;
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo[3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

Particular anticholinergic compounds that may be of use include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

The invention thus provides, in a further aspect, a combination comprising a compound of formula (I) or a pharmaceutically acceptable salt thereof, together with a PDE4 inhibitor.

The invention thus provides, in a further aspect, a combination comprising a compound of formula (I) or a pharmaceutically acceptable salt thereof, together with a 2-adrenoreceptor agonist.

The invention thus provides, in a further aspect, a combination comprising a compound of formula (I) or a pharmaceutically acceptable salt thereof, together with an anticholinergic.

The invention thus provides, in a further aspect, a combination comprising a compound of formula (I) or a pharmaceutically acceptable salt thereof, together with an anti-inflammatory agent (such as those classes of compounds described herein).

The invention thus provides, in a further aspect, a combination comprising a compound of formula (I) or a pharmaceutically acceptable salt thereof, together with a corticosteroid, such as fluticasone propionate or 6α,9α-difluoro-17α-[(2-furanylcarbonyl)oxy]-11β-hydroxy-16α-methyl-3-oxo-androsta-1,4-diene-17β-carbothioic acid S-fluoromethyl ester or mometasone furoate. Such combinations may be of particular interest for intranasal administration.

The invention thus provides, in a further aspect, a combination comprising a compound of formula (I) or a pharmaceutically acceptable salt thereof, together with a A2a receptor agonist, such as those compounds described in PCT/EP/2005/005651, such as (2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol].

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. Suitably, the individual compounds will be administered simultaneously in a combined pharmaceutical composition. Appropriate doses of known therapeutic agents will be readily appreciated by those skilled in the art.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The compounds of the invention may be prepared by the methods described below or by similar methods. Thus, the following Intermediates and Examples serve to illustrate preparation of compounds of the invention, and are not to be considered as limiting the scope of the invention in any way.

BRIEF DESCRIPTION OF THE DRAWINGS

FIG. 1 depicts an X-Ray pattern for the hydrochloride salt of 3-(4-{[4-(4-{[3-(3, 3-dimethyl-1-piperidinyl)propyl]oxy}phenyl)-1-piperidinyl]carbonyl}-1-naphthalenyl) propanoic acid (of example 3).

FIG. 2 depicts a DSC Thermogram of the hydrochloride salt of 3-(4-{[4-(4-{[3-(3, 3-dimethyl-1-piperidinyl)propyl]oxy}phenyl)-1-piperidinyl]carbonyl}-1-naphthalenyl) propanoic acid (of example 3). An endotherm with an onset temperature of approximately 164° C., due to sample melt, is shown.

GENERAL EXPERIMENTAL

Throughout the intermediates and examples, the following abbreviations may be used:
DCM: dichloromethane
DIPEA: N,N-diisopropylethylamine
DMF: N,N-dimethylformamide
EtOAc: ethyl acetate
EtOH: ethanol
h: hour(s)
HBTU: O-(benzotriazol-1-yl)-N,N,N',N'-tetramethyluronium hexafluorophosphate
HCl: hydrochloric acid
HPLC: High Performance Liquid Chromatography
L: litres
LCMS: Liquid Chromatography Mass Spectrometry
MDAP: mass directed autopreparative HPLC purification
MeOH: methanol
min: minute(s)
ml: millilitres
NaCl: sodium chloride
$NaHCO_3$: sodium hydrogencarbonate
NaOH: sodium hydroxide
NMP: 1-methyl-2-pyrrolidinone
RT: retention time
TBTU: O-(benzotriazol-1-yl)-N,N,N',N'-tetramethyluronium tetrafluoroborate
THF: tetrahydrofuran Flash silica gel refers to Merck Art No. 9385; silica gel refers to Merck Art No. 7734.

SCX cartridges are Ion Exchange SPE columns where the stationary phase is polymeric benzene sulfonic acid. These may be used to isolate amines.

SCX2 cartridges are Ion Exchange SPE columns where the stationary phase is polymeric propylsulfonic acid. These may be used to isolate amines.

Organic solutions may be dried for example either over magnesium sulphate or sodium sulphate.

Reactions may be carried out under nitrogen, if desired.

LCMS was conducted on a Supelcosil LCABZ+PLUS column (3.3 cm×4.6 mm ID) eluting with 0.1% $HCO_2H$ and 0.01M ammonium acetate in water (solvent A) and 0.05% $HCO_2H$ 5% water in acetonitrile (solvent B), using the following elution gradient 0.0-7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).

The Flashmaster II is an automated multi-user flash chromatography system, available from Argonaut Technologies Ltd, which utilises disposable, normal phase, SPE cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength uv-detector and two Gilson FC204 fraction-collectors enabling automated peak cutting, collection and tracking.

The XRPD method which was employed to analyse crystalline forms of compounds is as follows:

| | |
|---|---|
| Manufacturer | PANalytical - The Netherlands |
| Instrument | X'Pert Pro |
| Diffractometer Type | DY1850 |
| Tube anode | Cu |
| K-Alpha1 wavelength (A °) | 1.54056 |
| K-Alpha2 wavelength (A °) | 1.54439 |
| Ration Alpha 1:2 | 0.50000 |
| Divergence slit | Prog. Div. Slit |
| Receiving slit | Prog. Rec. Slit |
| Generator voltage (kV) | 40 |
| Tube Current (mA) | 45 |
| Detector | X'celerator |
| Data Angle range (°2θ) | 2.0-40.0 |
| Scan type | Continuous |
| Scan step size | 0.0167 |
| Scan step time (seconds) | 190.5 |
| Sample preparation | Flush Silicon wafer |

XRPD analysis was performed on a PANalytical X'Pert Pro X-ray powder diffractometer, model X' Pert Pro PW3040/60, serial number DY1850 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 190.5 seconds. The sample was prepared by mounting a few milligrams of sample on a Silicon wafer (zero background) plates, resulting in a thin layer of powder. Peak positions were measured using Highscore software.

DSC thermograms were obtained using a TA Q1000 calorimeter, serial number 1000-0126. The sample was weighed into an aluminium pan, a pan lid placed on top and lightly crimped without sealing the pan. The experiment was conducted using a heating rate of 10° C. min$^{-1}$.

Intermediate 1

1-[(3-Chloropropyl)oxy]-4-iodobenzene

A mixture of p-iodophenol (20 g, 91 mmol), potassium carbonate (25.2 g, 182 mmol) and 1-bromo-3-chloropropane (commercially available, for example, from Aldrich) (18 g, 114 mmol) in anhydrous 2-butanone (300 ml) was heated at reflux for 72 h, cooled to room temperature, filtered and evaporated to dryness. The resulting residue was purified by SPE filtration (70 g silica cartridge, eluting with 20:1 cyclohexane-ethyl acetate) to afford the title compound (24.9 g); $^1$H NMR (CDCl$_3$) δ 7.5 (2H, d), 6.7 (2H, d), 4.1 (2H, t), 3.8 (2H, t), 2.2 (2H, q).

Intermediate 2

1-{3-[(4-Iodophenyl)oxy]propyl}-3,3-dimethylpiperidine

A mixture of 1-[(3-chloropropyl)oxy]-4-iodobenzene (for example, as prepared for Intermediate 1) (6.5 g, 20 mmol), 3,3-dimethyl piperidine (commercially available, for example from Alfa) (3.39 g, 30 mmol), sodium iodide (2.99 g, 20 mmol) and potassium carbonate (3.3 g, 20 mmol) in anhydrous acetonitrile (100 ml) was heated at reflux overnight. The mixture was allowed to cool to room temperature, evaporated to dryness and quenched with water and extracted with dichloromethane, dried, filtered and concentrated to afford the title compound (8 g). LCMS RT=2.37 min, ES+ve m/z 374 (M+H)$^+$.

Intermediate 3

1,1-Dimethylethyl 4-(4-{[3-(3,3-dimethyl-1-piperidinyl)propyl]oxy}phenyl)-4-hydroxy-1-piperidinecarboxylate A solution of 1-{3-[(4-iodophenyl)oxy]propyl}-3,3-dimethylpiperidine (for example as prepared for Intermediate 2) (3 g, 8.02 mmol) in anhydrous THF (30 ml) was cooled to −78° C. under nitrogen and treated with "BuLi (1.6M solution in hexanes, 6.02 ml, 9.63 mmol), after 0.5 h, a solution of N-Boc-4-oxopiperidine (commercially available, for example from Aldrich) (1.99 g, 10 mmol) in THF (10 ml) was added dropwise. The mixture was allowed to warm up to room temperature and was stirred overnight. The mixture was quenched with ammonium chloride solution and extracted with EtOAc, dried over magnesium sulphate, filtered and concentrated. The resulting residue was purified by Flash-Master II chromatography using a 100 g cartridge, eluting with 100% cyclohexane for 5 minutes, 100% cyclohexane to 100% EtOAc over 15 minutes, 100% EtOAc to 100% DCM in 5 minutes and 100% DCM to 30% MeOH (containing 1% of triethylamine) in DCM over 40 minutes then held constant for 5 min, monitoring at 254 nm to afford the title compound (1.25 g). LCMS RT=2.48 min, ES+ve m/z 447 (M+H)$^+$.

Intermediate 4

3-Dimethyl-1-(3-{[4-(4-piperidinyl)phenyl]oxy}propyl)piperidine dihydrochloride

A solution of 1,1-dimethylethyl 4-(4-{[3-(3,3-dimethyl-1 piperidinyl)propyl]oxy}phenyl)-4-hydroxy-1-piperidinecarboxylate (for example as prepared for Intermediate 3) (1.25 g, 2.8 mmol) in anhydrous DCM (10 ml) was treated with triethylsilane (2.2 ml, 13.7 mmol) and stirred at room temperature under nitrogen for 0.5 h. The solution was cooled to −78° C. and trifluoroacetic acid (3 ml) was added. The reaction was allowed to warm up to room temperature and stirred overnight. The mixture was evaporated to dryness, and co-evaporated with toluene twice. The resulting residue was purified on a SCX-2 cartridge (20 g) eluting with MeOH, followed by 2M ammonia solution in MeOH to afford a yellow thick oil which was treated with 2M hydrogen chloride in ether, evaporated to afford the title compound (886 mg), containing some 4-(4-{[3-(3,3-dimethyl-1-piperidinyl)propyl]oxy}phenyl)-1,2,3,6-tetrahydropyridine dichloride, so an aliquot of this mixture (0.54 g) was hydrogenated in EtOH (15 ml) at room temperature using 10% wt palladium on carbon (0.5 g) at atmospheric pressure over 2 h. The catalyst was removed by filtration through Celite, washed with ethanol and the filtrate was evaporated to dryness to afford the title compound (448 mg). LCMS RT=1.77 min, ES+ve m/z 331 (M+H)$^+$.

Intermediate 5

4-[(1E)-3-(Methyloxy)-3-oxo-1-propen-1-yl]-1-naphthalenecarboxylic acid a) A mixture of 4-bromo-1-naphthalenecarboxylic acid (which may be prepared by the methods described in Can. J. Chem. 1981, 59, 2629-41) (100 mg, 0.4 mmol), triethylamine (0.42 ml, 3 mmol), palladium acetate (12 mg, 0.04 mmol), triphenylphosphine (13 mg, 0.04 mmol) and methyl acrylate (1.19 ml, 0.11 mmol) in anhydrous DMF (8 ml) was heated to 100° C. for 4 h under nitrogen. The mixture was allowed to cool to room temperature, evaporated to dryness under reduced pressure and purified by aminopropyl cartridge, eluting with MeOH, followed by 4M HCl in dioxane and then 2M ammonia in MeOH. The ammonia in methanol fractions were combined to afford a residue that was partitioned between DCM and water, the DCM layers combined, dried over magnesium sulfate filtered and evaporated to afford the title compound (99 mg, 97%). LCMS RT=3.25 min, ES−ve m/z 255 (M−H)⁻.

b) A mixture of 4-bromo-1-naphthalenecarboxylic acid (9.42 g), triethylamine (25 ml), palladium acetate (0.85 g), triphenylphosphine (0.98 g) and methyl acrylate (9.68 g) in anhydrous DMF (95 ml) was heated to 100° C. for 1 h under nitrogen. The mixture was allowed to cool to room temperature, filtered through Celite and washed with diethyl ether/water. The filtrate was extracted with ether, then with EtOAc. The aqueous phase was acidified to approximately pH 1 with 2 M aqueous hydrogen chloride. The solid was filtered, washed with water and dried at 40° C. under vacuum, to afford the title compound (8.2 g).

Intermediate 6

4-[3-(Methyloxy)-3-oxopropyl]-1-naphthalenecarboxylic acid a) 4-[(1E)-3-(Methyloxy)-3-oxo-1-propen-1-yl]-1-naphthalenecarboxylic acid (for example as prepared for Intermediate 5) (1.73 g, 5.09 mmol) is hydrogenated over palladium on carbon (10 wt %, 350 mg) in ethanol (50 ml) for 4 h. The catalyst is removed by filtration through Celite, and the mixture hydrogenated again with fresh catalyst (350 mg) overnight. The mixture is filtered through Celite and concentrated to afford the title compound.

b) 4-[(1E)-3-(Methyloxy)-3-oxo-1-propen-1-yl]-1-naphthalenecarboxylic acid (for example as prepared for Intermediate 5) (4 g, 5.09 mmol) in 500 mL ethanol was hydrogenated over palladium on carbon (10 wt %, 1 g) for about 2 h. The catalyst was removed by filtration through Celite, the solvent evaporated and the resultant solid left overnight under vacuum to afford the title compound (3.8 g). ES+ve m/z 258 (M+H)⁺.

Intermediate 7

Methyl 3-(4-{[4-(4-{[3-(3,3-dimethyl-1-piperidinyl)propyl]oxy}phenyl)-1-piperidinyl]carbonyl}-1-naphthalenyl)propanoate A solution of 4-[3-(methyloxy)-3-oxopropyl]-1-naphthalenecarboxylic acid (for example as prepared for Intermediate 6) (0.197 g, 0.76 mmol) in anhydrous DMF (2 ml) was treated with HBTU (0.29 g 0.77 mmol), diisopropylethylamine (0.6 ml, 3.82 mmol), the mixture was stirred at room temperature for 20 minutes, 3,3-dimethyl-1-(3-{[4-(4-piperidinyl)phenyl]oxy}propyl)piperidine dihydrochloride (for example as prepared for Intermediate 4) (250 mg, 0.63 mmol) was added and the mixture stirred at room temperature for 4 h. The mixture was evaporated to dryness and purified on a SCX-2 cartridge (5 g) eluting with MeOH, followed by 2M ammonia solution in methanol to afford the title compound (238 mg). LCMS RT=2.79 min, ES+ve m/z 571.

Example 1

3-(4-{[4-(4-{[3-(3,3-dimethyl-1-piperidinyl)propyl]oxy}phenyl)-1-piperidinyl]carbonyl}-1-naphthalenyl)propanoic acid, formic acid (1:1)

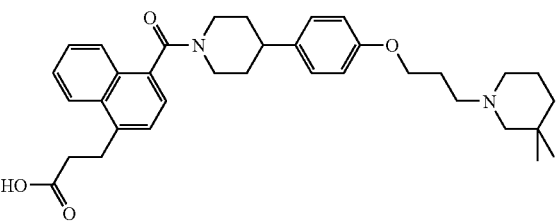

A mixture of methyl 3-(4-{[4-(4-{[3-(3,3-dimethyl-1-piperidinyl)propyl]oxy}phenyl)-1-piperidinyl]carbonyl}-1-naphthalenyl)propanoate (for example, as prepared in Intermediate 7) (238 mg, 0.42 mmol) and potassium hydroxide (117 mg, 2.08 mmol), in methanol (15 ml)—water (1 ml) was heated to reflux for approximately 2 h, cooled to room temperature, evaporated and the residue was purified by mass-directed auto-preparative HPLC to afford the title compound (60 mg). LCMS RT=2.73 min, ES+ve m/z 557 (M+H)⁺.

¹H NMR δ (250 MHz; DMSO-$d_6$, 120° C.) 8.19 (1H, s), 8.18-8.12 (1H, m), 7.89-7.82 (1H, m), 7.64-7.54 (2H, m), 7.44 (1H, d, J=7.5 Hz), 7.37 (1H, d, J=7.5 Hz), 7.18-7.12 (2H, m), 6.89-6.82 (2H, m), 4.02 (2H, t, J=6.5 Hz), 3.38 (2H, t, J=7.5 Hz), 3.10-2.97 (2H, m), 2.84-2.73 (1H, m), 2.69 (2H, t, J=7.5 Hz), 2.38 (2H, t, J=7.0 Hz), 2.34-2.27 (2H, m), 2.03 (2H, s), 1.90-1.74 (4H, m), 1.66-1.48 (4H, m), 1.23-1.17 (2H, m), 0.92 (6H, s).

Example 2

3-(4-{[4-(4-{[3-(3,3-dimethyl-1-piperidinyl)propyl]oxy}phenyl)-1-piperidinyl]carbonyl}-1-naphthalenyl)propanoic acid, free base Compound may be prepared in accordance with the following reaction schemes:

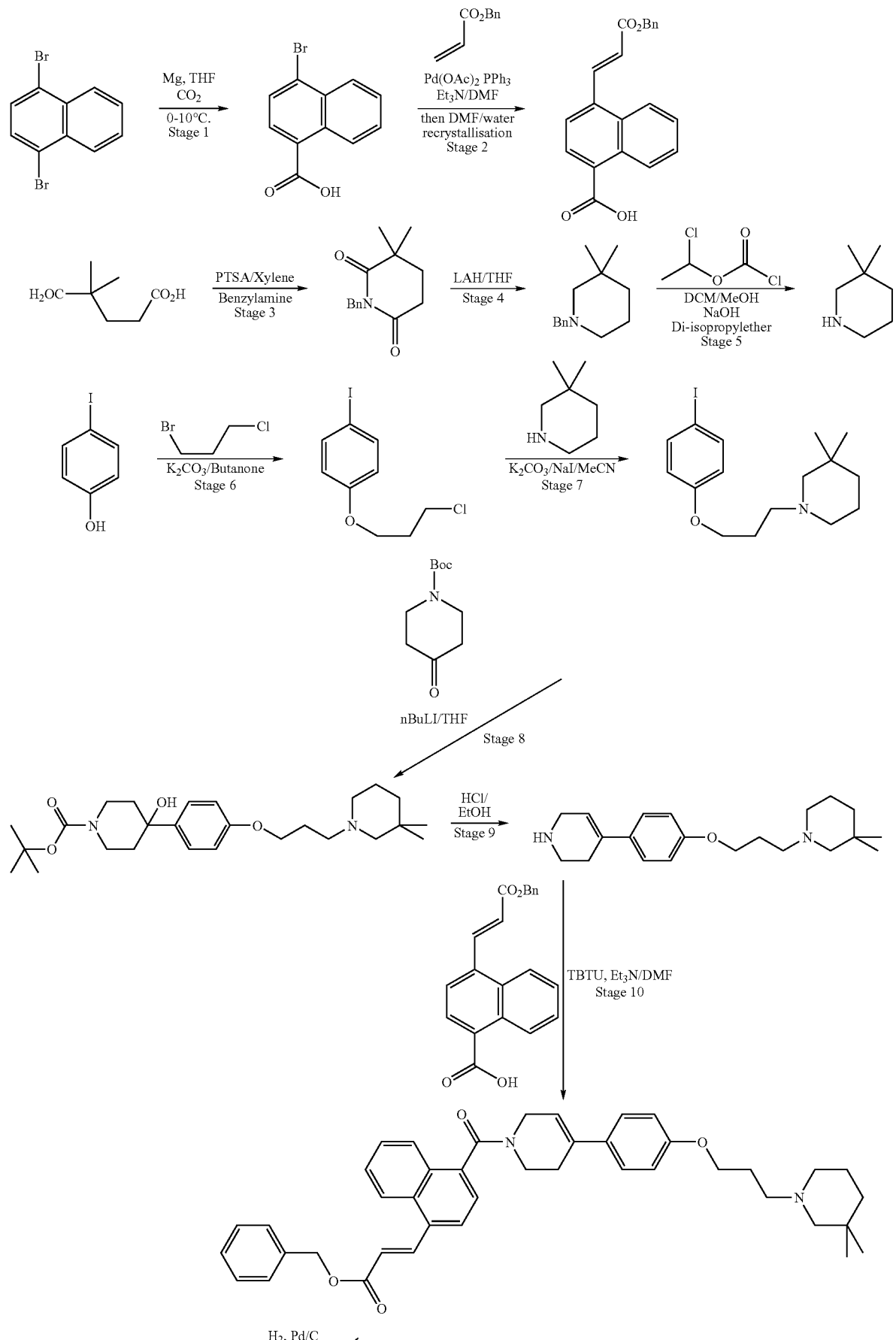

in which
Bn represents benzyl
BOC represents t-butoxycarbonyl

Intermediate 8

Stage 0

1,4-Dibromonaphthalene

A solution of bromine (120.9 ml, 3 eqv) in chloroform (400 ml) is added over 6 h to a solution of naphthalene (100 g) in chloroform (200 ml) and DMF (19 ml) at 0-10° C. The reaction is stirred at 0-30° C. (for example 20-30° C.) for up to about 24 h and then chloroform (100 ml) is added. The reaction mixture is washed with aqueous sodium bisulphite (1×600 ml), then washed with 5% aqueous sodium bicarbonate (1×300 ml), then water (300 ml), then evaporated. The residue is crystallised from methanol (2600 ml), by heating to 65-70° C., and cooling to 20-30° C. for 3-4 h. The product is filtered, and dried under vacuum at 50-55° C. (dry weight 117 g).

Intermediate 9

Stage 1

4-Bromo-1-naphthalenecarboxylic acid

A solution of 1,4-dibromonaphthalene (100 g) in THF (500 ml) is added to magnesium (8.49 g) and iodine (trace) in THF (200 ml) over about 2 h and heated at 65-75° C. for up to 7 h (typically 3-4 h) to prepare a solution of the Grignard reagent. The solution is cooled to 0-10° C. and carbon dioxide gas is passed through the solution for 10-16 h. Water (100 ml) is added slowly, and after stirring for about 30 min at 0-10° C., is acidified (typically to pH 2-3) with hydrochloric acid. The THF layer is separated off, and concentrated. The residue is added to aqueous sodium carbonate (20%, 500 ml) and washed with toluene (2×200 ml). The aqueous solution is treated with hydrochloric acid (typically to pH 2-3). The product is filtered off, washed with water, and dried under vacuum at about 90-100° C. for about 12 h (dry weight 60 g).

Intermediate 10

Stage 2

4-{(1E)-3-Oxo-3-[(phenylmethyl)oxy]-1-propen-1-yl}-1-naphthalenecarboxylic acid A mixture of 4-bromo-1-naphthalenecarboxylic acid (100 g), benzylacrylate (96.8 g), triphenylphosphine (10.2 g) palladium(II) acetate (2 g), triethylamine (258 ml) and DMF (600 ml) are heated at 90-100° C. for 4-12 h (typically 10-12 h). Two further portions of palladium(II) acetate (20 g) are added at four hour intervals during the stir period. The mixture is treated with charcoal (3×15 g) at 50-80° C. (typically 70-80° C.) filtering after each charge at 40-45° C. The DMF is then distilled off at 80-90° C. under vacuum and the residue is cooled to 25-35° C. Dichloromethane (100 ml) and water (100 ml) are added to the residue and the mixture is acidified with concentrated hydrochloric acid and is stirred at 20-35° C. for about 30 min. The mixture is filtered, and the solid product dried. The residue is dissolved in a mixture of DMF (600 ml) then water (400 ml) at 90-100° C. and stirred for 1-1.5 h. The solution is filtered at 80-85° C., cooled to 20-35° C., and stirred for about 2 h. The product is filtered off and dried (dry weight 43 g).

Intermediate 11

Stage 3

3,3-Dimethyl-1-(phenylmethyl)-2,6-piperidinedione

A solution of dimethylglutaric acid (250 g) in xylene (1.87 L) is treated with p-toluene sulphonic acid (5.9 g) and heated at reflux. A solution of benzylamine (165.5 g) in xylene (6 ml) is added over about 2 h, and reflux is continued for about 24 h, removing water azeotropically throughout. The mixture is cooled, and the solvent is removed by distillation under reduced pressure to leave the desired product (dry weight 321 g).

Intermediate 12

Stage 4

3,3-Dimethyl-1-(phenylmethyl)piperidine

A solution of 3,3-dimethyl-1-(phenylmethyl)-2,6-piperidinedione (200 g) in THF (400 ml) is added over 1-4 h (for example 1-2 h) at −5 to +5° C. to a solution of lithium aluminium hydride (68 g) in THF (2 L). The mixture is then heated to 20-35° C. for about 1-2 h, and then to reflux for 24-30 h. The mixture is then cooled to −5 to +5° C. and ethyl acetate (280 ml) is added slowly, followed by aqueous sodium sulphate (257 g in water 1.4 L) and further ethyl acetate (1 L). The mixture is stirred at 25-35° C. for about 1 h. The organic layer is filtered through a Hyflow bed, washing with ethyl acetate (2×2 L). The filtrate layers are combined, then washed with brine (1 L) and evaporated to give the product. The product may be further purified by column chromatography, eluting with petroleum ether and ethyl acetate mixtures or by fractional distillation (dry weight 105 g).

Intermediate 13

Stage 5

3,3-Dimethylpiperidine

To a solution of 1-chloroethylchloroformate (94.6 g) in dichloromethane (560 ml) cooled to 0-15° C. (typically 0-5° C., is added 3,3-dimethyl-1-(phenylmethyl)piperidine (112 g) over 15 min and the reaction mixture stirred for about 1 h, allowing to warm to 20-30° C. The reaction is heated at reflux for 2-20 h (for example about 2 h), then the solvent removed in vacuo. Methanol (560 ml) is added to the residue at 5-30° C. (typically 20-30° C.) then the mixture is heated at reflux for 3-20 h (for example 3-4 h) then cooled to 5-30° C. and concentrated. Diethyl ether (400 ml) and isopropanol (20 ml) are added, then the mixture is stirred at 25-35° C. for 30 min-2 h. The solid material is filtered off and washed with diethyl ether (200 ml). The solid is dissolved in water (336 ml) and diethyl ether (560 ml), and then 10M sodium hydroxide (200 ml) is added at 20-30° C. The layers are separated and the aqueous layer is extracted with diethyl ether (560 ml). The combined ether solutions are concentrated and the product is purified by fractional distillation (dry weight 41 g).

Intermediate 1

Stage 6

1-[(3-Chloropropyl)oxy]-4-iodobenzene

A mixture of 4-iodophenol (250 g), potassium carbonate (313.6 g) and 2-butanone (1500 ml) is stirred for 15-20 min. 1-bromochloropropane (357.71 g) is added over about 10 minutes at 25-30° C. After stirring for a further 10 min, the reaction mass is heated to reflux (about 80-85° C.) for 22-24 h. After cooling to 25-30° C., the mixture is filtered, washing the cake with 2-butanone (750 ml). The filtrate is concentrated under reduced pressure at 50-60° C. Ethyl acetate (3750 ml) is added and stirred for 10-20 min to get a clear solution. This is washed with 2N sodium hydroxide solution (1250 ml), water (2500 ml) and aqueous sodium chloride (2500 ml) and then dried with sodium sulfate. The solvent is concentrated under reduced pressure at 50-60° C. n-heptane (250 ml) is added and stirred for about 20 min at 25-30° C. The solution is then cooled to −5 to −10° C. and stirred for about 30 min. The solid is filtered, washed with chilled n-heptane (125 ml, 0-5° C.) and the solid is allowed to dry.

Second Crop Isolation:

The combined filtrate and washings are concentrated and n-heptane (70 ml) is added and the mixture stirred for about 20 min at 25-30° C. The solution is cooled to −5 to −10° C., stirred for about 35 min and the solid is filtered and washed with chilled n-heptane (30 ml, 0-5° C.). Products from both crops were dried at 35-40° C. under vacuum for 6-10 h, to give the title compound (285 g).

Intermediate 2

Stage 7

1-{3-[(4-Iodophenyl)oxy]propyl}-3,3-dimethylpiperidine

A mixture of 1-[(3-chloropropyl)oxy]-4-iodobenzene (100 g) and acetonitrile (600 ml) is stirred for about 5 min at 25-35° C., then potassium carbonate (93.07 g) followed by 3,3-dimethylpiperidine (49.53 g) are added over about 10 min. Potassium iodide (2.24 g) is added, then the mixture is stirred for about 15 min, before being heated to 78-82° C. for 22-24 h. The reaction mixture is cooled to 25-35° C., and the solid residue is filtered and washed with acetonitrile (200 ml). The filtrate and washings are concentrated under reduced pressure at 50-60° C. to give a thick liquid which is stirred with n-heptane (100 ml) for about 30 min at 25-30° C. The solution is then cooled to −5 to 10° C. and stirred for about 30 min. The solid is filtered, washed with chilled n-heptane (50 ml, 0-5° C.), then dried at 35-40° C. under vacuum for 6-10 h to give the title compound (97 g).

Second Crop Isolation:

The combined filtrate and washings are concentrated to a thick syrup and n-heptane (50 ml) is added and stirred for about 20 min at 25-30° C. The solution is cooled to −5 to −10° C., stirred for about 40 min, then the solid is filtered and washed with chilled n-heptane (40 ml, 0-5° C.). The solid is dried at 35-40° C. under vacuum for 6-10 h to give the title compound. The total dry weight of title compound (from first and second crops) is 92.1 g.

Intermediate 3

Stage 8

1,1-Dimethylethyl 4-(4-{[3-(3,3-dimethyl-1-piperidinyl)propyl]oxy}phenyl)-4-hydroxy-1-piperidinecarboxylate A solution of 1-{3-[(4-iodophenyl)oxy]propyl}-3,3-dimethylpiperidine (25 g) in THF (125 ml) is stirred for about 15 min, then cooled to 0-5° C. Isopropyl magnesium chloride solution (70.5 ml, 1.9M) is added at 0-5° C. over about 40 min, then the mixture is stirred at 0-5° C. for 2-3 h. The mixture is then cooled to −78 to −80° C. and a precooled solution (−20 to −30° C.) of N-Boc-piperidinone (16 g) in THF (125 ml) is added over about 1-2 h and the reaction mixture is stirred for about 1.5 h at −78 to −80° C. The reaction mixture is allowed to warm to 25-30° C., then stirred for 23-24 h. Saturated ammonium chloride solution (375 ml) is added at 25-30° C., followed by ethyl acetate (500 ml) and the mixture stirred for about 50 min. The aqueous layer is extracted with ethyl acetate (250 ml). The combined organic layers are washed with water (375 ml), dried over sodium sulfate and concentrated under reduced pressure to give the crude title compound (30.3 g).

Intermediate 14

Stage 9

4-(4-{[3-(3,3-Dimethyl-1-piperidinyl)propyl]oxy}phenyl)-1,2,3,6-tetrahydropyridine A mixture of crude 1,1-dimethylethyl-4-(4-{[3-(3,3-dimethyl-1-piperidinyl)propyl]oxy}phenyl)-4-hydroxy-1-piperidinecarboxylate (100 g) in 95% ethanol (500 ml) is cooled to 5-10° C. and concentrated hydrogen chloride (300 ml) is added at 5-10° C. over about 45 min, then stirred for about 15 min. The mixture is then heated to reflux (about 80-85° C.) for about 6 h. The mixture is concentrated under vacuum at 50-60° C., then water (500 ml) is added. The mixture is then cooled to 5-10° C. and the pH adjusted to pH 10-12 with 2N sodium hydroxide solution at 5-10° C. The mixture is warmed to 25-35° C., and extracted with ethyl acetate (500 ml, then 2×200 ml). The combined ethyl acetate layers are washed with water (200 ml), then 10% aqueous sodium chloride solution (200 ml). The solvent is removed under vacuum and the product is purified by column chromatography (100-200 mesh silica gels) using a linear gradient of MeOH/DCM 0-70% to give the title compound (21.7 g).

Intermediate 15

Stage 10

Phenylmethyl (2E)-3-(4-{[4-(4-{[3-(3,3-dimethyl-1-piperidinyl)propyl]oxy}phenyl)-3,6-dihydro-1(2H)-pyridinyl]carbonyl}-1-naphthalenyl)-2-propanoate A mixture of 4-{(1E)-3-oxo-3-[(phenylmethyl)oxy]-1-propen-1-yl}-1-naphthalenecarboxylic acid (63.3 g) in ethyl acetate (570 ml) is stirred at 25-35° C. for 10-15 min. Triethylamine (73.6 g) is added over about 10 min at 25-35° C., followed by TBTU (61.2 g) over about 5 min at 25-35° C. The mixture is stirred for about 35 min and then cooled to 0-10° C. A solution of 4-(4-{[3-(3,3-dimethyl-1-piperidinyl)propyl]oxy}phenyl)-1,2,3,6-tetrahydropyridine (57 g) in ethyl acetate (570 ml) is added over about 15 min at 0-10° C., and stirred for about 15 min. The temperature is raised slowly to 25-35° C. and stirred for 2.5-3.5 h. Ethyl acetate (570 ml) and saturated sodium hydrogen carbonate solution (570 ml) are added and stirred for about 70 min at 25-35° C. The aqueous layer is separated and the ethyl acetate layer is washed with water (570 ml) and aqueous sodium chloride solution (570 ml). The organic layer is concentrated under reduced pressure below about 55° C. to give a thick liquid. Acetone (114 ml) is added and the solution is cooled to 25-35° C. and stirred for about 20 min. n-Heptane (114 ml) is added slowly and the mixture is then cooled to 0-5° C., stirred for about 60 min and the solid is filtered and washed with chilled n-heptane (57 ml). The solid is dried under vacuum at 35-40° C. to give the title compound (47 g).

Example 2

Stage 11

3-(4-{[4-(4-{[3-(3,3-dimethyl-1-piperidinyl)propyl]oxy}phenyl)-1-piperidinyl]carbonyl}-1-naphthalenyl)propanoic acid, free base A solution of phenylmethyl-(2E)-3-(4-{[4-(4-{[3-(3,3-dimethyl-1-piperidinyl)propyl]oxy}phenyl)-3,6-dihydro-1(2H)-pyridinyl]carbonyl}-1-naphthalenyl)-2-propanoate (47 g) in methanol (705 ml) is added to a hydrogenation flask. 10% Pd/C (11.75 g, 50% moist) is added and the mixture heated to 40-45° C. under 60-70 psi hydrogen pressure and shaken for about 2-3 h. The reaction mixture is cooled to 25-30° C., and filtered through Celite, washing with MeOH (235 ml). The filtrate is concentrated under vacuum at a temperature below about 60° C. to give the title compound (37.2 g). NMR analysis confirmed the compound to be the title compound.

Example 3

3-(4-{[4-(4-{[3-(3,3-dimethyl-1-piperidinyl)propyl]oxy}phenyl)-1-piperidinyl]carbonyl}-1-naphthalenyl)propanoic acid, hydrochloride salt 3-(4-{[4-(4-{[3-(3,3-dimethyl-1-piperidinyl)propyl]oxy}phenyl)-1-piperidinyl]carbonyl}-1-naphthalenyl)propanoic acid (321.2 g) was added over 5-10 min to isopropanol (1.93 L) at 30-35° C. under nitrogen and stirred at about 300-400 rpm. Further isopropanol (1.61 L) was added and the mixture warmed to 65-70° C. to give a solution, which was then cooled to 40-45° C. and stirred at about 300 rpm. Concentrated hydrochloric acid (50 ml) was added over about 1 h and after about 40 min, a seed of authentic 3-(4-{[4-(4-{[3-(3,3-dimethyl-1-piperidinyl)propyl]oxy}phenyl)-1-piperidinyl]carbonyl}-1-naphthalenyl)propanoic acid, hydrochloride salt (1.6 g) was added as a slurry in isopropanol (about 10-12 ml). The mixture was then cooled to about 15° C. over about 4 h. The mixture was then stirred at this temperature overnight. The suspension was filtered, washing the solid with isopropanol (1.2 L and 0.6 L), then the solid was pulled dry for about 4 h, then dried under vacuum for 21 h at 50-60° C. to give the title compound (dry weight 236 g).

The seed was prepared as follows: The freebase (300 mg) was dissolved in isopropanol (3.3 ml) with heating. Concentrated hydrogen chloride (37%, 0.0465 ml, 1.05 equivalents) was added to the freebase solution at ambient temperature. The reaction was left to temperature cycle (0-40° C.) over a weekend. The white solid was isolated, washed with isopropanol and air dried for about 2 h before drying in the vacuum oven overnight at 40° C. (weight 137 mg)

A representative XRPD pattern for the hydrochloride salt of 3-(4-{[4-(4-{[3-(3,3-dimethyl-1-piperidinyl)propyl]oxy}phenyl)-1-piperidinyl]carbonyl}-1-naphthalenyl)propanoic acid (Example 3) is shown in FIG. 1.

The peak angles are tabulated below.

| 2θ/° | d-spacing/Å |
| --- | --- |
| 2.2 | 39.7 |
| 4.2 | 20.8 |
| 6.3 | 14.0 |
| 8.4 | 10.5 |
| 10.5 | 8.4 |
| 12.6 | 7.0 |
| 15.5 | 5.7 |
| 16.0 | 5.5 |
| 17.0 | 5.2 |
| 18.1 | 4.9 |
| 18.4 | 4.8 |
| 18.9 | 4.7 |
| 20.9 | 4.2 |
| 22.4 | 4.0 |
| 25.6 | 3.5 |
| 25.9 | 3.4 |
| 26.8 | 3.3 |

A representative DSC thermogram for the hydrochloride salt of 3-(4-{[4-(4-{[3-(3,3-dimethyl-1-piperidinyl)propyl]oxy}phenyl)-1-piperidinyl]carbonyl}-1-naphthalenyl)propanoic acid (Example 3) is shown in FIG. 2 with a melt of approximately 164° C.

Biological Data

Compounds of the invention may be tested for in vitro and/or in vivo biological activity, for example in accordance with the following or similar assays:

H1 Receptor Cell Line Generation and FLIPR Assay Protocol
1. Generation of Histamine H1 Cell Line The human H1 receptor may be cloned using known procedures described in the literature [*Biochem. Biophys. Res. Commun.*, 201(2):894 (1994)]. Chinese hamster ovary (CHO) cells stably expressing the human H1 receptor may be generated according to known procedures described in the literature [*Br. J. Pharmacol.*, 117(6):1071 (1996)].

Histamine H1 Functional Antagonist Assay: Determination of Functional pKi Values The histamine H1 cell line is seeded into non-coated black-walled clear bottom 384-well tissue culture plates in alpha minimum essential medium (Gibco/Invitrogen, cat no. 22561-021), supplemented with 10% dialysed foetal calf serum (Gibco/Invitrogen cat no. 12480-021) and 2 mM L-glutamine (Gibco/Invitrogen cat no 25030-024) and is maintained overnight at 5% $CO_2$, 37° C.

Excess medium is removed from each well to leave 10 μl. 30 μl loading dye (250 μM Brilliant Black, 2 μM Fluo-4 diluted in Tyrodes buffer+probenecid (145 mM NaCl, 2.5 mM KCl, 10 mM HEPES, 10 mM D-glucose, 1.2 mM $MgCl_2$, 1.5 mM $CaCl_2$, 2.5 mM probenecid, pH adjusted to 7.40 with NaOH 1.0 M)) is added to each well and the plates are incubated for 60 min at 5% $CO_2$, 37° C.

10 μl of test compound, diluted to the required concentration in Tyrodes buffer+probenecid (or 10 μl Tyrodes buffer+probenecid as a control) is added to each well and the plate incubated for 30 min at 37° C., 5% $CO_2$. The plates are then placed into a FLIPR™ (Molecular Devices, UK) to monitor cell fluorescence ($\lambda_{ex}$=488 nm, $\lambda_{EM}$=540 nm) in the manner described in Sullivan et al., (In: Lambert D G (ed.), *Calcium*

Signaling Protocols, New Jersey: Humana Press, 1999, 125-136) before and after the addition of 10 µl histamine at a concentration that results in the final assay concentration of histamine being $EC_{80}$.

Functional antagonism is indicated by a suppression of histamine induced increase in fluorescence, as measured by the FLIPR™ system (Molecular Devices). By means of concentration effect curves, functional affinities are determined using standard pharmacological mathematical analysis.

Histamine H1 Functional Antagonist Assay: Determination of Antagonist pA2

The histamine H1 receptor expressing CHO cells is seeded into non-coated black-walled clear bottom 96-well tissue culture plates as described above.

Following overnight culture, growth medium is removed from each well, washed with 200 µl phosphate buffered saline (PBS) and replaced with 50 µl loading dye (250 µM Brilliant Black, 1 µM Fluo-4 diluted in Tyrodes buffer+probenecid (145 mM NaCl, 2.5 mM KCl, 10 mM HEPES, 10 mM D-glucose, 1.2 mM $MgCl_2$, 1.5 mM $CaCl_2$, 2.5 mM probenecid, pH adjusted to 7.40 with NaOH 1.0 M)). Cells are incubated for 45 min. at 37° C. The loading buffer is removed and the cells washed as above, and 90 µl of Tyrodes buffer+probenecid is added to each well. 10 µl of test compound, diluted to the required concentration in Tyrodes buffer+probenecid (or 10 µl Tyrodes buffer+probenecid as a control) is added to each well and the plate incubated for 30 min at 37° C., 5% $CO_2$.

The plates are then placed into a FLIPR™ (Molecular Devices, UK) to monitor cell fluorescence ($\lambda_{ex}$=488 nm, $\lambda_{EM}$=540 nm) in the manner described in Sullivan et al., (In: Lambert D G (ed.), Calcium Signaling Protocols, New Jersey: Humana Press, 1999, 125-136) before and after the addition of 50 µl histamine over a concentration range of 1 mM-0.1 nM. The resultant concentration response curves are analysed by non-linear regression using a standard four parameter logistic equation to determine the histamine EC50, the concentration of histamine required to produce a response of 50% of the maximum response to histamine. The antagonist pA2 is calculated using the following standard equation: pA2=log(DR−1)−log [B] where DR=dose ratio, defined as EC50antagonist-treated/EC50control and [B]=concentration of antagonist.

2. H3 Receptor Cell Line Generation, Membrane Preparation and Functional GTPγS Assay Protocols
Generation of Histamine H3 Cell Line The histamine H3 cDNA is isolated from its holding vector, pcDNA3.1 TOPO (InVitrogen), by restriction digestion of plasmid DNA with the enzymes BamH1 and Not-1 and ligated into the inducible expression vector pGene (InVitrogen) digested with the same enzymes. The GeneSwitch™ system (a system wherein transgene expression is switched off in the absence of an inducer and switched on in the presence of an inducer) is performed as described in U.S. Pat. Nos. 5,364,791; 5,874,534; and 5,935,934. Ligated DNA is transformed into competent DH5α E. coli host bacterial cells and plated onto Luria Broth (LB) agar containing Zeocin™ (an antibiotic which allows the selection of cells expressing the sh ble gene which is present on pGene and pSwitch) at 50 µgml$^{-1}$. Colonies containing the re-ligated plasmid are identified by restriction analysis. DNA for transfection into mammalian cells is prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) are seeded at 2×10$^6$ cells per T75 flask in Complete Medium, containing Hams F12 (GIBCOBRL, Life Technologies) medium supplemented with 10% v/v dialysed foetal bovine serum, L-glutamine, and hygromycin (100 µgml$^{-1}$), 24 h prior to use. Plasmid DNA is transfected into the cells using Lipofectamine plus according to the manufacturers guidelines (InVitrogen). 48 h post transfection cells are placed into complete medium supplemented with 500 µgml$^{-1}$ Zeocin™.

10-14 days post selection, 10 nM Mifepristone (InVitrogen) is added to the culture medium to induce the expression of the receptor. 18 h post induction, cells are detached from the flask using ethylenediamine tetra-acetic acid (EDTA; 1:5000; InVitrogen), following several washes with phosphate buffered saline pH 7.4 and are then resuspended in Sorting Medium containing Minimum Essential Medium (MEM), without phenol red, and supplemented with Earles salts and 3% Foetal Clone II (Hyclone). Approximately 1×10$^7$ cells are examined for receptor expression by staining with a rabbit polyclonal antibody, 4a, raised against the N-terminal domain of the histamine H3 receptor, incubated on ice for 60 min, followed by two washes in sorting medium. Receptor bound antibody is detected by incubation of the cells for 60 min on ice with a goat anti rabbit antibody, conjugated with Alexa 488 fluorescence marker (Molecular Probes). Following two further washes with Sorting Medium, cells are filtered through a 50 µm Filcon™ (BD Biosciences) and are then analysed on a FACS Vantage SE Flow Cytometer fitted with an Automatic Cell Deposition Unit, Control cells are non-induced cells treated in a similar manner. Positively stained cells are sorted as single cells into 96-well plates, containing Complete Medium containing 500 µgml$^{-1}$ Zeocin™ and allowed to expand before reanalysis for receptor expression via antibody and ligand binding studies. Clone, 3H3, is selected for membrane preparation.

Membrane Preparation from Cultured Cells

All steps of the protocol are carried out at 4° C. and with pre-cooled reagents. The cell pellet is resuspended in 10 volumes of homogenisation buffer (50 mM N-2-hydroxyethylpiperazine-N'-2-ethanesulfonic acid (HEPES), 1 mM ethylenediamine tetra-acetic acid (EDTA), pH 7.4 with KOH, supplemented with 10$^{-6}$ M leupeptin (acetyl-leucyl-leucyl-arginal; Sigma L2884), 25 µgml$^{-1}$ bacitracin (Sigma B0125), 1 mM phenylmethylsulfonyl fluoride (PMSF) and 2×10$^{-6}$ M pepstain A (Sigma)). The cells are then homogenised by 2×15 second bursts in a 1 litre glass Waring blender, followed by centrifugation at 500 g for 20 min. The supernatant is then spun at 48,000 g for 30 min. The pellet is resuspended in homogenisation buffer (4× the volume of the original cell pellet) by vortexing for 5 seconds, followed by homogenisation in a Dounce homogeniser (10-15 strokes). At this point the preparation is aliquoted into polypropylene tubes and stored at −80° C.

Histamine H3 Functional Antagonist Assay

For each compound being assayed, in a solid white 384 well plate, is added:—

(a) 0.5 µl of test compound diluted to the required concentration in DMSO (or 0.5 µl DMSO as a control);

(b) 30 µl bead/membrane/GDP mix which is prepared by mixing Wheat Germ Agglutinin Polystyrene LeadSeeker® (WGA PS LS) scintillation proximity assay (SPA) beads with membrane (prepared in accordance with the methodology described above) and diluting in assay buffer (20 mM N'-2-hydroxyethylpiperazine-N'-2-ethanesulfonic acid (HEPES)+100 mM NaCl+10 mM $MgCl_2$, pH 7.4 NaOH) to give a final volume of 30l which contains 5 µg protein, 0.25 mg bead per well and 10 µM final assay concentration of guanosine 5' diphosphate (GDP) (Sigma, diluted in assay buffer) incubating at room temperature for 60 min on a roller;

(c) 15 μl 0.38 nM [$^{35}$S]-GTPγS (Amersham; Radioactivity concentration=37 MBqml$^{-1}$; Specific activity=1160 Cimmol$^{-1}$), histamine (at a concentration that results in the final assay concentration of histamine being EC$_{80}$).

After 2-6 h, the plate is centrifuged for 5 min at 1500 rpm and counted on a Viewlux counter using a 613/55 filter for 5 minplate$^{-1}$. Data is analysed using a 4-parameter logistical equation. Basal activity used as minimum, i.e. histamine not added to well.

In Vivo Anti-Inflammatory Wheal and Flare Model

Male Dunkin-Hartley guinea pigs 500 g-1 kg are dosed with test compound or vehicle using a 1 ml syringe into the oral cavity (0.5 ml/kg p.o.), or via a marginal ear vein (0.33 ml/kg i.v.). Compounds are formulated in 5% DMSO/45% PEG200/50% water.

Either 2 hr after oral or 15 min after intravenous compound administration, guinea pigs are anaesthetised with isoflurane (5%, 2-31/min O$_2$), and receive Evans blue solution (2% in saline), 0.33 ml/kg i.v. via a marginal ear vein.

Immediately after Evans blue administration, and whilst still under isoflurane, animals are placed in a prone position, and an area of the back shaved. Histamine (10 μg/100 μl×4) and vehicle (1×100 μl PBS) is injected intradermally into the shaved dorsal surface.

Following histamine challenge, the animals are allowed to recover from anaesthesia and, 30 minutes later are euthanased with an i.p. overdose of pentobarbitone. The dorsal skin is carefully removed and wheal areas (stained blue) measured from the inner skin surface by taking two perpendicular diameters using engineer's calipers, and calculating the average radius. This value is used to calculate the area of each wheal, and the mean value of all histamine-induced wheals is subsequently calculated for each animal. If Evans blue is seen in the vehicle-challenge wheal, then that animal is excluded from the data set.

Dose-response curves are constructed for each test compound and ID$_{50}$ values may be determined for each route of administration (oral and intravenous).

CNS Penetration (i) CNS Penetration by Bolus Administration

Compounds are dosed intravenously at a nominal dose level of 1 mg/kg to male CD Sprague Dawley rats. Compounds are formulated in 5% DMSO/45% PEG200/50% water. Blood samples are taken under terminal anaesthesia with isoflurane at 5 minutes post-dose and the brains are also removed for assessment of brain penetration. Blood samples are taken directly into heparinised tubes. Blood samples are prepared for analysis using protein precipitation and brain samples are prepared using extraction of drug from brain by homogenisation and subsequent protein precipitation. The concentration of parent drug in blood and brain extracts is determined by quantitative LC-MS/MS analysis using compound-specific mass transitions.

(ii) CNS Penetration Following Intravenous Infusion at Steady State

A loading dose of the compounds is given to male CD Sprague Dawley rats at a nominal dose level of 0.4 mg/kg. The compounds are then infused intravenously for four hours at a nominal dose level of 0.1 mg/kg/h. Compounds are formulated in 2% DMSO/30% PEG200/68% water. Serial or terminal blood samples are taken at 0.5, 1.5, 2.5, 3, 3.5 and 4 hours post dose. The final blood sample is collected under terminal anaesthesia with isoflurane and the brains are also removed for assessment of brain penetration. Blood samples are taken directly into heparinised tubes. Blood samples are prepared for analysis using protein precipitation and brain samples are prepared using extraction of drug from brain by homogenisation and subsequent protein precipitation. The concentration of parent drug in blood and brain extracts is determined by quantitative LC-MS/MS analysis using compound-specific mass transitions.

Rat Pharmacokinetics

Compounds are dosed to male CD Sprague Dawley rats by single intravenous or oral administration at a nominal dose level of 1 mg/kg and 3 mg/kg respectively. Compounds are formulated in 5% DMSO/45% PEG200/50% water. An intravenous profile is obtained by taking serial or terminal blood samples at 0.083, 0.25, 0.5, 1, 2, 4, and 7 hours post dose (for some studies 12 and 24 hour samples may be taken). An oral profile is obtained by taking serial or terminal blood samples at 0.25, 0.5, 1, 2, 4, 7 and 12 hours post dose (for some studies 24 and 30 hour samples may be taken). Blood samples are taken directly into heparinised tubes. Blood samples are prepared by protein precipitation and subjected to quantitative analysis by LC-MS/MS using compound-specific mass transitions. Drug concentration-time profiles are generated and non-compartmental PK analysis used to generate estimates of half-life, clearance, volume of distribution and oral bioavailability.

Dog Pharmacokinetics

Compounds are dosed to male Beagle dogs by single intravenous or oral administration at a nominal dose level of 1 mg/kg and 2 mg/kg respectively. The study is carried out according to a crossover design such that the same dog is used for both dosing events and the dosing events occurred 1 week apart. Compounds are formulated in 5% DMSO/45% Peg200/50% water. An intravenous profile is obtained by taking serial blood samples at 0.083, 0.25, 0.5, 0.75, 1, 2, 4, 6 and 12 hr post dose (for some studies 24 hour samples may be taken). An oral profile is obtained by taking serial blood samples at 0.25, 0.5, 0.75, 1, 2, 4, 6, 12 and 24 hr post dose. Blood samples are taken directly into heparinised tubes. Blood samples are prepared by protein precipitation and subjected to quantitative analysis by LC-MS/MS using compound-specific mass transitions. Drug concentration-time profiles are generated and non-compartmental PK analysis used to generate estimates of half-life, clearance, volume of distribution and oral bioavailability.

Results

In these or similar assays, the compound of Examples 1 and 3, had (i) an average pKi (pKb) at H3 of approximately 7.4 for Example 1 and 7.3 for Example 3

(ii) an average pKi (pKb) at H1 of approximately 7.8 for Example 1 and 7.9 for Example 3, and a pA2 of about 8.1 for Example 3

(iii) anti-inflammatory activity in vivo (in the wheal and flare model an ID$_{50}$ of about 0.6 mg/Kg i.v. and about 2.8 mg/Kg oral (Example 3)

(iv) oral bioavailability in the rat and the dog (about 59% in the rat for Example 1, and combined data for Example 1 and 3 of about 60% in the dog)

(v) low plasma clearance in the rat and the dog (Example 1a half-life of about 4-5 hours (IV route) in the rat), and combined data for Example 1 and 3a half-life of approximately 3 hours in the dog)

(vi) low CNS penetration, less than 50 ng/gm (Example 1 and 3).

What is claimed is:

1. A compound of formula (I)

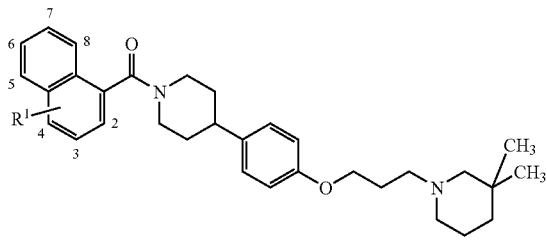

(I)

wherein
the naphthalene ring is substituted in the 2, 3, 4, 5, 6, 7 or 8 position by $R^1$, and $R^1$ represents —$CH_2CH_2COOH$ or —CH=C($CH_3$)COOH; or
a salt thereof.

2. A compound of formula (I) according to claim 1 in which the naphthalene ring is substituted in the 2, 3, 4, 5, 6, 7 or 8 position by $R^1$, and $R^1$ represents —$CH_2CH_2COOH$; or a salt thereof.

3. A compound of formula (I) according to claim 1, wherein the compound is in the form of a pharmaceutically acceptable salt.

4. 3-(4-{[4-(4-{[3-(3,3-dimethyl-1-piperidinyl)propyl]oxy}phenyl)-1-piperidinyl]carbonyl}-1-naphthalenyl)propanoic acid, or a salt thereof.

5. A compound according to claim 4 in the form of the free base.

6. A compound according to claim 4 in the form of a pharmaceutically acceptable salt.

7. A compound according to claim 6 in the form of a hydrochloride salt.

8. A composition which comprises a compound of formula (I)

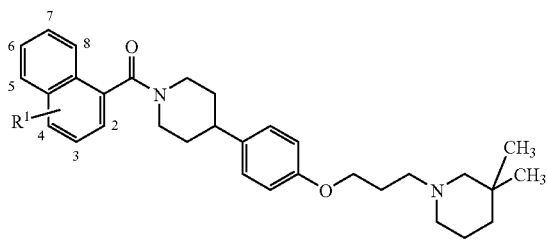

(I)

wherein
the naphthalene ring is substituted in the 2, 3, 4, 5, 6, 7 or 8 position by $R^1$, and $R^1$ represents —$CH_2CH_2COOH$ or —CH=C($CH_3$)COOH; or
a pharmaceutically acceptable salt thereof, and one or more pharmaceutically acceptable carriers and/or excipients.

9. A composition according to claim 8 wherein the compound of formula (I) comprises 3-(4-{[4-(4-{[3-(3,3-dimethyl-1-piperidinyl)propyl]oxy}phenyl)-1-piperidinyl]carbonyl}-1-naphthalenyl)propanoic acid, or a pharmaceutically acceptable salt thereof.

10. A composition according to claim 9 wherein the 3-(4-{[4-(4-{[3-(3,3-dimethyl-1-piperidinyl)propyl]oxy}phenyl)-1-piperidinyl]carbonyl}-1-naphthalenyl)propanoic acid is in the form of a hydrochloride salt.

11. A composition according to claim 8, 9, or 10 adapted for oral delivery.

12. A composition according to claim 8, 9, or 10 in the form of a capsule, tablet, powder, granules, solution or suspension in aqueous or non-aqueous liquids, edible foam or whip, an oil-in-water liquid emulsion or a water-in-oil liquid emulsion.

13. A method for the treatment of allergic rhinitis which comprises administering to a patient in need thereof an effective amount of a compound of formula (I)

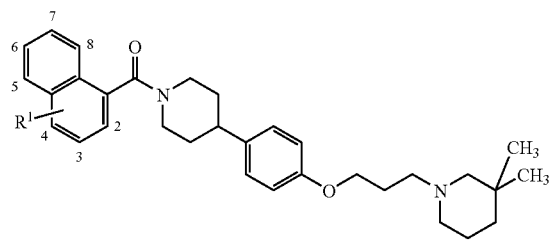

(I)

wherein
the naphthalene ring is substituted in the 2, 3, 4, 5, 6, 7 or 8 position by $R^1$, and $R^1$ represents —$CH_2CH_2COOH$ or —CH=C($CH_3$)COOH; or
a pharmaceutically acceptable salt thereof.

14. A method for the treatment according to claim 13, wherein the compound of formula (I) is 3-(4-{[4-(4-{[3-(3,3-dimethyl-1-piperidinyl)propyl]oxy}phenyl)-1-piperidinyl]carbonyl}-1-naphthalenyl)propanoic acid, or a pharmaceutically acceptable salt thereof.

15. A method for the treatment according to claim 14, wherein the 3-(4-{[4-(4-{[3-(3,3-dimethyl-1-piperidinyl)propyl]oxy}phenyl)-1-piperidinyl]carbonyl}-1-naphthalenyl)propanoic acid is in the form of a hydrochloride salt.

16. A method for the treatment according to claim 13, 14 or 15, wherein the compound is administered orally.

* * * * *